(12) United States Patent
Rauch et al.

(10) Patent No.: US 6,642,358 B1
(45) Date of Patent: Nov. 4, 2003

(54) RECEPTOR THAT BINDS TRAIL

(75) Inventors: Charles Rauch, Bainbridge Island, WA (US); Henning Walczak, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 09/578,392

(22) Filed: May 25, 2000

Related U.S. Application Data

(60) Division of application No. 08/883,036, filed on Jun. 26, 1997, now Pat. No. 6,072,047, which is a continuation-in-part of application No. 08/869,852, filed on Jun. 4, 1997, now abandoned, which is a continuation-in-part of application No. 08/829,536, filed on Mar. 28, 1997, now abandoned, which is a continuation-in-part of application No. 08/815,255, filed on Mar. 12, 1997, now abandoned, which is a continuation-in-part of application No. 08/799,861, filed on Feb. 13, 1997, now abandoned.

(51) Int. Cl.$^7$ .................. C07K 14/00; C07K 21/04; C12N 15/00
(52) U.S. Cl. ............ 530/350; 530/300; 435/69.1; 435/7.1; 435/320.1; 435/325; 435/252.3; 435/172.3; 536/23.1; 536/23.5
(58) Field of Search .................. 530/300, 350; 435/69.1, 7.1, 320.1, 325, 252.3, 172.3; 536/23.1, 23.5

(56) References Cited

U.S. PATENT DOCUMENTS

| | | | |
|---|---|---|---|
| 5,763,223 A | 6/1998 | Wiley et al. ............ 435/69.5 |
| 6,313,269 B1 | * 11/2001 | Deen et al. |
| 6,342,369 B1 | * 1/2002 | Ashkenazi |
| 6,417,328 B2 | * 7/2002 | Alnemri |
| 2002/0072091 A1 | * 6/2002 | Ni et al. |

FOREIGN PATENT DOCUMENTS

| | | |
|---|---|---|
| EP | 870827 | 10/1998 |
| WO | WO 98/32856 | 7/1998 |
| WO | WO 98/41629 | 9/1998 |
| WO | WO 98/46643 | 10/1998 |
| WO | WO 98/51793 | 11/1998 |
| WO | WO 99/02653 | 1/1999 |
| WO | WO 99/09165 | 2/1999 |
| WO | WO 99/12963 | 3/1999 |

OTHER PUBLICATIONS

U.S. patent application Ser. No. 60/041,230, Deen et al., filed Mar. 14, 1997.
U.S. patent application Ser. No. 08/853,684, Deen et al., filed May 9, 1997.
U.S. patent application Ser. No. 08/916,625, Deen et al., filed Aug. 22, 1997.
U.S. patent application Ser. No. 60/040,846, Ni et al., filed Mar. 17, 1997.
Berger et al., "Guide to Molecular Cloning Techniques, Methods in Enzymology," Academic Press, Inc., 152:661–663, 1987.
Bowie et al., "Deciphering the Message in Protein Sequences: Tolerance to Amino Acid Substitutions," Science, 247:1306–1310, 1990.
Cross et al., "Purification of CpG Islands Using a Methylated DNA Binding Column," Nature Genetics, 6:236–244, 1994.
U.S. patent application Ser. No. 60/054,021, Ni et al., filed Jul. 29, 1997.
U.S. patent application Ser. No. 08/843,652, Holtzman, filed Apr. 16, 1997.
U.S. patent application Ser. No. 08/857,216, Ashkenazi, filed May 15, 1997.
U.S. patent application Ser. No. 09/020,746, Ashkenazi et al., filed Feb. 9, 1998.
U.S. patent application Ser. No. 60/055,906, Alnemri, filed Aug. 15, 1997.
U.S. patent application Ser. No. 60/058,631, Tschopp, filed Sep. 12, 1997.
U.S. patent application Ser. No. 60/084,422, Tschopp et al., filed May 6, 1998.
Database record for Accession No. AA223122, "zr06g05.r1, Stratagene NT2 Neuronal Precursor 937230 Homo Sapiens cDNA Clone 650744 5' mRNA Sequence", Submitted by R.K. Wilson Feb. 19, 1997.
George et al., "Current Methods in Sequence Comparison and Analysis," in Macromolecular Sequencing and Synthesis, Selected Methods and Applications, Edited by David H. Schlesinger, Alan R. Liss, Inc., New York, pp. 127–149, 1988.
MacDonald et al., "H. Sapiens CpG Island DNA Genomic MseI Fragment, Clone 75a7, Reverse Read cpg75a7.rtla," Locus HS75A7R, databank record for Accession No. Z66083, Oct. 1995.
Pan et al., "The Receptor for the Cytotoxic Ligand TRAIL", Science 276:111, Apr. 4, 1997.
White et al., "Principles of Biochemistry," 6:155–158, McGraw–Hill, Inc., 1978.
R.K. Wilson, Databank record for GenBank Accession No. AA232440; submitted Feb. 28, 1997; released Mar. 13, 1998.

* cited by examiner

Primary Examiner—Gary Kunz
Assistant Examiner—Nirmal Basi
(74) Attorney, Agent, or Firm—Julie K. Smith; Kathryn A. Anderson; Stuart Watt

(57) ABSTRACT

A protein designated TRAIL receptor binds the protein known as TNF-Related Apoptosis-Inducing Ligand (TRAIL). The TRAIL receptor finds use in purifying TRAIL or inhibiting activities thereof. Isolated DNA sequences encoding TRAIL-R polypeptides are provided, along with expression vectors containing the DNA sequences, and host cells transformed with such recombinant expression vectors. Antibodies that are immunoreactive with TRAIL-R are also provided.

41 Claims, 3 Drawing Sheets

FIGURE 1

```
    CTGAGACTCTGAGACAGTGCTTCGATGACTTTGCAGACTTGGTGCCCTTTGACTCCTGGG    60
1   ----------+---------+---------+---------+---------+---------+
    GACTCTGAGACTCTGTCACGAAGCTACTGAAACGTCTGAACCACGGGAAACTGAGGACCC

E  T  L  R  Q  C  F  D  D  F  A  D  L  V  P  F  D  S  W  E  -

AGCCGGCTCATGAGGAAGTTGGGCCTCATGGACAATGAGATAAAGGTGGCTAAAGCTGAGG   120
61  ----------+---------+---------+---------+---------+---------+
    TCGGCGAGTACTCCTTCAACCCGGAGTACCTGTTACTCTATTTCCACCGATTTCGACTCC

P  L  M  R  K  L  G  L  M  D  N  E  I  K  V  A  K  A  E  A  -

CAGCGGGGCCACAGGGACACCTTGTNCACNATGCTGAT   157
121 ----------+---------+---------+--------
    GTCGCCCCGGTGTCCCTGTGGAACANGTGNTACGACTA

A  G  H  R  D  T  L  X  T  M  L  -
```

RECEPTOR THAT BINDS TRAIL

CROSS-REFERENCE TO RELATED APPLICATIONS

This application is a divisional of application Ser. No. 08/883,036, filed Jun. 26, 1997, now U.S. Pat. No. 6,072,047, which is a continuation-in-part of application Ser. No. 08/869,852, filed Jun. 4, 1997, now abandoned, which is a continuation-in-part of application Ser. No. 08/829,536, filed Mar. 28, 1997, now abandoned, which is a continuation-in-part of application Ser. No. 08/815,255, filed Mar. 12, 1997, now abandoned, which is a continuation-in-part of application Ser. No. 08/799,861, filed Feb. 13, 1997, now abandoned.

BACKGROUND OF THE INVENTION

A protein known as TNF-related apoptosis-inducing ligand (TRAIL) is a member of the tumor necrosis factor family of ligands (Wiley et al., *Immunity*, 3:673–682, 1995). TRAIL has demonstrated the ability to induce apoptosis of certain transformed cells, including a number of different types of cancer cells as well as virally infected cells (PCT application WO 97/01633 and Wiley et al., supra).

Identification of receptor protein(s) that bind TRAIL would prove useful in further study of the biological activities of TRAIL. However, prior to the present invention, no receptor for TRAIL had been reported.

SUMMARY OF THE INVENTION

The present invention is directed to a novel protein designated TRAIL receptor (TRAIL-R), which binds to a protein known as TNF-related apoptosis-inducing ligand (TRAIL). DNA encoding TRAIL-R, and expression vectors comprising such DNA, are provided. A method for producing TRAIL-R polypeptides comprises culturing host cells transformed with a recombinant expression vector encoding TRAIL-R, under conditions that promote expression of TRAIL-R, then recovering the expressed TRAIL-R polypeptides from the culture. Antibodies that are immunoreactive with TRAIL-R are also provided.

BRIEF DESCRIPTION OF THE DRAWINGS

FIG. 1 presents the nucleotide sequence of a human TRAIL receptor DNA fragment, SEQ ID NO:3 as well as the amino acid sequence encoded thereby SEQ ID NO:4. This DNA fragment is described in Example 3.

DETAILED DESCRIPTION OF THE INVENTION

Figure 2:
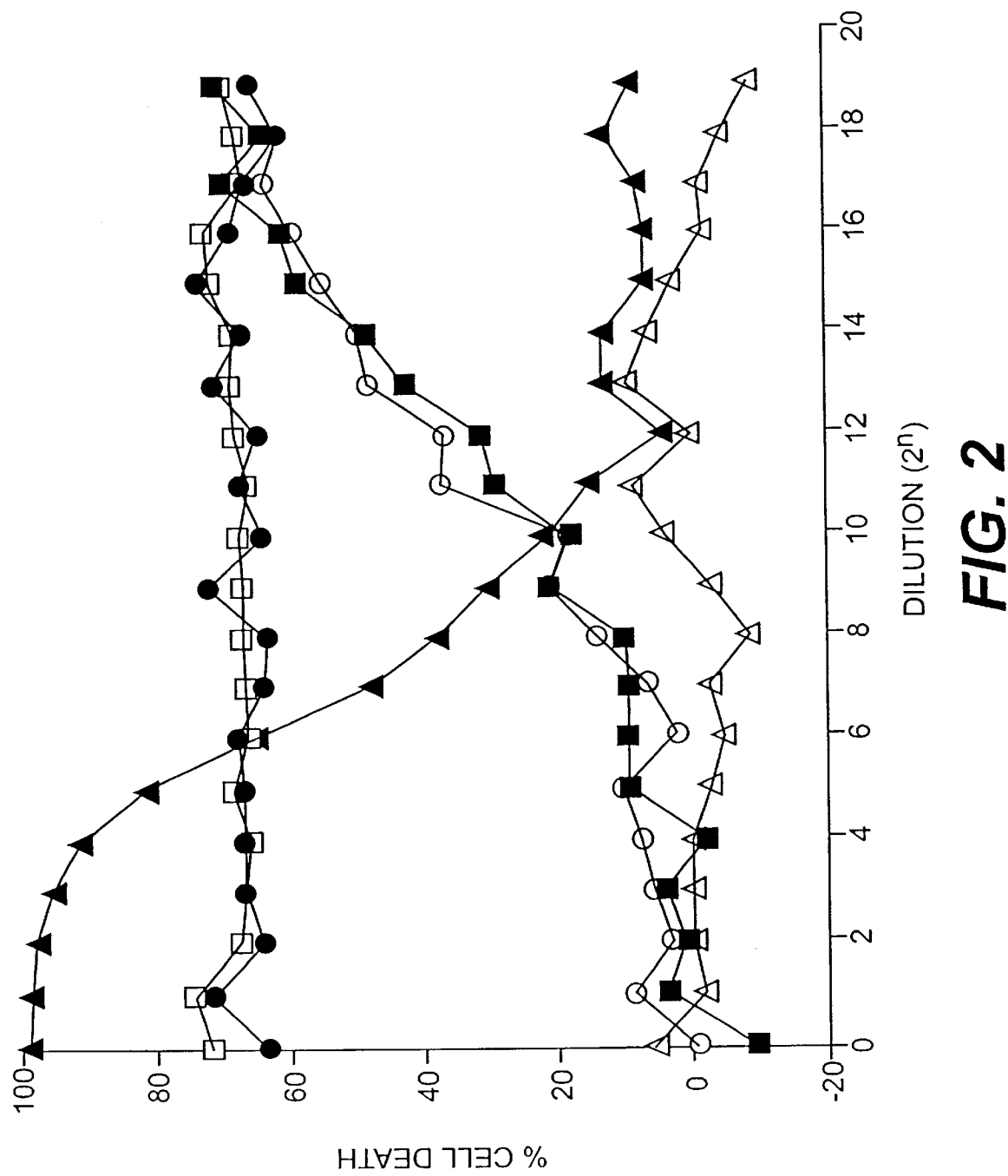
FIG. 2 presents the results of the assay described in example 7. In the assay, a soluble TRAIL-R/Fc fusion protein blocked TRAIL-induced apoptosis of Jurkat cells.

A novel protein designated TRAIL receptor (TRAIL-R) is provided herein. TRAIL-R binds to the cytokine designated TNF-related apoptosis-inducing ligand (TRAIL). Certain uses of TRAIL-R flow from this ability to bind TRAIL, as discussed further below. TRAIL-R finds use in inhibiting biological activities of TRAIL, or in purifying TRAIL by affinity chromatography, for example.

The nucleotide sequence of the coding region of a human TRAIL receptor DNA is presented in SEQ ID NO:1. The amino acid sequence encoded by the DNA sequence of SEQ ID NO:1 is shown in SEQ ID NO:2. This sequence information identifies the TRAIL receptor protein as a member of the tumor necrosis factor receptor (TNF-R) family of receptors (reviewed in Smith et al., *Cell* 76:959–962, 1994). The extracellular domain contains cysteine rich repeats; such motifs have been reported to be important for ligand binding in other receptors of this family. TRAIL-R contains a so-called "death domain" in the cytoplasmic region; such domains in certain other receptors are associated with transduction of apoptotic signals. These and other features of the protein are discussed in more detail below.

TRAIL-R protein or immunogenic fragments thereof may be employed as immunogens to generate antibodies that are immunoreactive therewith. In one embodiment of the invention, the antibodies are monoclonal antibodies.

A human TRAIL-R protein was purified as described in example 1. In example 2, amino acid sequence information derived from fragments of TRAIL-R is presented. One embodiment of the invention is directed to a purified human TRAIL-R protein that is capable of binding TRAIL, wherein the TRAIL-R is characterized as comprising the amino acid sequence VPANEGD (amino acids 327 to 333 of SEQ ID NO:2). In another embodiment, the TRAIL-R additionally comprises the sequence ETLRQCFDDFADLVPFDSWE-PLMRKLGLMDNEIKVAKAEAAGHRDTLXTML (amino acids 336 to 386 of SEQ ID NO:2, with one unknown amino acid indicated as X). Also provided are TRAIL-R fragments comprising only one of these characterizing amino acid sequences.

The nucleotide sequence of a TRAIL-R DNA fragment, and the amino acid sequence encoded thereby, are presented in FIG. 1 (SEQ ID NO:3 and SEQ ID NO:4); see example 3. The amino acid sequence presented in FIG. 1 has characteristics of the so-called "death domains" found in the cytoplasmic region of certain other receptor proteins. Such domains have been reported to be associated with transduction of apoptotic signals. Cytoplasmic death domains have been identified in Fas antigen (Itoh and Nagata, *J. Biol. Chem.* 268:10932, 1993), TNF receptor type I (Tartaglia et al. *Cell* 74:845, 1993), DR3 (Chinnaiyan et al., *Science* 274:990–992, 1996), and CAR-1 (Brojatsch et al., *Cell* 87:845–855, 1996). The role of these death domains in initiating intracellular apoptotic signaling cascades is discussed further below.

SEQ ID NO:1 presents the nucleotide sequence of the coding region of a human TRAIL receptor DNA, including an initiation codon (ATG) and a termination codon (TAA). The amino acid sequence encoded by the DNA of SEQ ID NO:1 is presented in SEQ ID NO:2. The fragment depicted in FIG. 1 corresponds to the region of TRAIL-R that is presented as amino acids 336 to 386 in SEQ ID NO:2.

The TRAIL-R protein of SEQ ID NO:2 includes an N-terminal hydrophobic region that functions as a signal peptide, followed by an extracellular domain, a transmembrane region comprising amino acids 211 through 231, and a C-terminal cytoplasmic domain. Computer analysis predicts that the signal peptide corresponds to residues 1 to 51 of SEQ ID NO:2. Cleavage of the signal peptide thus would yield a mature protein comprising amino acids 52 through 440 of SEQ ID NO:2. The calculated molecular weight for a mature protein containing residues 52 to 440 of SEQ ID NO:2 is about 43 kilodaltons. The next most likely computer-predicted signal peptidase cleavage sites (in descending order) occur after amino acids 50 and 58 of SEQ ID NO:2.

In another embodiment of the invention, the N-terminal residue of a mature TRAIL-R protein is the isoleucine residue at position 56 of SEQ ID NO:2. Sequences of several tryptic digest peptide fragments of TRAIL-R were determined by a combination of N-terminal sequencing and Nano-ES MS/MS (nano electrospray tandem mass spectrometry). The N-terminal amino acid of one of the peptide fragments was the isoleucine at position 56 of SEQ ID NO:2. Since this fragment was not preceded by a trypsin cleavage site, the (Ile)56 residue may correspond to the N-terminal residue resulting from cleavage of the signal peptide.

A further embodiment of the invention is directed to mature TRAIL-R having amino acid 54 as the N-terminal residue. In one preparation of TRAIL-R (a soluble TRAIL-R/Fc fusion protein expressed in CV1-EBNA cells), the signal peptide was cleaved after residue 53 of SEQ ID NO:2.

The skilled artisan will recognize that the molecular weight of particular preparations of TRAIL-R protein may differ, according to such factors as the degree of glycosylation. The glycosylation pattern of a particular preparation of TRAIL-R may vary according to the type of cells in which the protein is expressed, for example. Further, a given preparation may include multiple differentially glycosylated species of the protein. TRAIL-R polypeptides with or without associated native-pattern glycosylation are provided herein. Expression of TRAIL-R polypeptides in bacterial expression systems, such as *E. coli*, provides non-glycosylated molecules.

In one embodiment, the protein is characterized by a molecular weight within the range of about 50 to 55 kilodaltons, which is the molecular weight determined for a preparation of native, full length, human TRAIL-R. Molecular weight can be determined by SDS-polyacrylamide gel electrophoresis (SDS-PAGE).

Example 1 presents one method for purifying a TRAIL-R protein. Jurkat cells are disrupted, and the subsequent purification process includes affinity chromatography (employing a chromatography matrix containing TRAIL), and reversed phase HPLC.

TRAIL-R polypeptides of the present invention may be purified by any suitable alternative procedure, using known protein purification techniques. In one alternative procedure, the chromatography matrix instead comprises an antibody that binds TRAIL-R. Other cell types expressing TRAIL-R (e.g., the PS-1 cells described in example 2) can be substituted for the Jurkat cells. The cells can be disrupted by any of the numerous known techniques, including freeze-thaw cycling, sonication, mechanical disruption, or by use of cell lysing agents.

The desired degree of purity depends on the intended use of the protein. A relatively high degree of purity is desired when the protein is to be administered in vivo, for example. Advantageously, TRAIL-R polypeptides are purified such that no protein bands corresponding to other (non-TRAIL-R) proteins are detectable upon analysis by SDS-polyacrylamide gel electrophoresis (SDS-PAGE). It will be recognized by one skilled in the pertinent field that multiple bands corresponding to TRAIL-R protein may be visualized by SDS-PAGE, due to differential glycosylation, differential post-translational processing, and the like. TRAIL-R most preferably is purified to substantial homogeneity, as indicated by a single protein band upon analysis by SDS-PAGE. The protein band may be visualized by silver staining, Coomassie blue staining, or (if the protein is radiolabeled) by autoradiography.

The present invention encompasses TRAIL-R in various forms, including those that are naturally occurring or produced through various techniques such as procedures involving recombinant DNA technology. Such forms of TRAIL-R include, but are not limited to, fragments, derivatives, variants, and oligomers of TRAIL-R, as well as fusion proteins containing TRAIL-R or fragments thereof.

TRAIL-R may be modified to create derivatives thereof by forming covalent or aggregative conjugates with other chemical moieties, such as glycosyl groups, lipids, phosphate, acetyl groups and the like. Covalent derivatives of TRAIL-R may be prepared by linking the chemical moieties to functional groups on TRAIL-R amino acid side chains or at the N-terminus or C-terminus of a TRAIL-R polypeptide. Conjugates comprising diagnostic (detectable) or therapeutic agents attached to TRAIL-R are contemplated herein, as discussed in more detail below.

Other derivatives of TRAIL-R within the scope of this invention include covalent or aggregative conjugates of TRAIL-R polypeptides with other proteins or polypeptides, such as by synthesis in recombinant culture as N-terminal or C-terminal fusions. Examples of fusion proteins are discussed below in connection with TRAIL-R oligomers. Further, TRAIL-R-containing fusion proteins can comprise peptides added to facilitate purification and identification of TRAIL-R. Such peptides include, for example, poly-His or the antigenic identification peptides described in U.S. Pat. No. 5,011,912 and in Hopp et al., *Bio/Technology* 6:1204, 1988. One such peptide is the Flag® peptide, Asp-Tyr-Lys-Asp-Asp-Asp-Asp-Lys, which is highly antigenic and provides an epitope reversibly bound by a specific monoclonal antibody, enabling rapid assay and facile purification of expressed recombinant protein. A murine hybridoma designated 4E11 produces a monoclonal antibody that binds the Flag® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the Flag® peptide are available from Eastman Kodak Co., Scientific Imaging Systems Division, New Haven, Conn.

Both cell membrane-bound and soluble (secreted) forms of TRAIL-R are provided herein. Soluble TRAIL-R may be identified (and distinguished from non-soluble membrane-bound counterparts) by separating intact cells expressing a TRAIL-R polypeptide from the culture medium, e.g., by centrifugation, and assaying the medium (supernatant) for the presence of the desired protein. The presence of TRAIL-R in the medium indicates that the protein was secreted from the cells and thus is a soluble form of the desired protein.

Soluble forms of receptor proteins typically lack the transmembrane region that would cause retention of the protein on the cell surface. In one embodiment of the invention, a soluble TRAIL-R polypeptide comprises the extracellular domain of the protein. A soluble TRAIL-R polypeptide may include the cytoplasmic domain, or a portion thereof, as long as the polypeptide is secreted from the cell in which it is produced. One example of a soluble TRAIL-R is a soluble human TRAIL-R comprising amino acids 52 to 210 of SEQ ID NO:2. Other soluble TRAIL-R polypeptides include, but are not limited to, polypeptides comprising amino acids x to 210 of SEQ ID NO:2, wherein x is an integer from 51 through 59.

Soluble forms of TRAIL-R possess certain advantages over the membrane-bound form of the protein. Purification of the protein from recombinant host cells is facilitated, since the soluble proteins are secreted from the cells. Further, soluble proteins are generally more suitable for certain applications, e.g., for intravenous administration.

TRAIL-R fragments are provided herein. Such fragments may be prepared by any of a number of conventional techniques. Desired peptide fragments may be chemically synthesized. An alternative involves generating TRAIL-R fragments by enzymatic digestion, e.g., by treating the protein with an enzyme known to cleave proteins at sites defined by particular amino acid residues. Yet another suitable technique involves isolating and amplifying a DNA fragment encoding a desired polypeptide fragment, by polymerase chain reaction (PCR). Oligonucleotides that define the desired termini of the DNA fragment are employed as the 5' and 3' primers in the PCR.

Examples of fragments are those comprising at least 20, or at least 30, contiguous amino acids of the sequence of SEQ ID NO:2. Fragments derived from the cytoplasmic domain find use in studies of TRAIL-R-mediated signal transduction, and in regulating cellular processes associated with transduction of biological signals. TRAIL-R polypeptide fragments also may be employed as immunogens, in generating antibodies. Particular embodiments are directed to TRAIL-R polypeptide fragments that retain the ability to bind TRAIL. Such a fragment may be a soluble TRAIL-R polypeptide, as described above.

Naturally occurring variants of the TRAIL-R protein of SEQ ID NO:2 are provided herein. Such variants include, for example, proteins that result from alternate mRNA splicing events or from proteolytic cleavage of the TRAIL-R protein. Alternate splicing of mRNA may, for example, yield a truncated but biologically active TRAIL-R protein, such as a naturally occurring soluble form of the protein. Variations attributable to proteolysis include, for example, differences in the N- or C-termini upon expression in different types of host cells, due to proteolytic removal of one or more terminal amino acids from the TRAIL-R protein (generally from 1–5 terminal amino acids). TRAIL-R proteins in which differences in amino acid sequence are attributable to genetic polymorphism (allelic variation among individuals producing the protein) are also contemplated herein.

The skilled artisan will also recognize that the position(s) at which the signal peptide is cleaved may differ from that predicted by computer program, and may vary according to such factors as the type of host cells employed in expressing a recombinant TRAIL-R polypeptide. A protein preparation may include a mixture of protein molecules having different N-terminal amino acids, resulting from cleavage of the signal peptide at more than one site. As discussed above, particular embodiments of mature TRAIL-R proteins provided herein include, but are not limited to, proteins having the residue at position 51, 52, 54, 56, or 59 of SEQ ID NO:2 as the N-terminal amino acid.

Regarding the discussion herein of various domains of TRAIL-R protein, the skilled artisan will recognize that the above-described boundaries of such regions of the protein are approximate. To illustrate, the boundaries of the transmembrane region (which may be predicted by using computer programs available for that purpose) may differ from those described above. Thus, soluble TRAIL-R polypeptides in which the C-terminus of the extracellular domain differs from the residue so identified above are contemplated herein.

Other naturally occurring TRAIL-R DNAs and polypeptides include those derived from non-human species. Homologs of the human TRAIL-R of SEQ ID NO:2, from other mammalian species, are contemplated herein, for example. Probes based on the human DNA sequence of SEQ ID NO:3 or SEQ ID NO:1 may be used to screen cDNA libraries derived from other mammalian species, using conventional cross-species hybridization techniques.

TRAIL-R DNA sequences may vary from the native sequences disclosed herein. Due to the known degeneracy of the genetic code, wherein more than one codon can encode the same amino acid, a DNA sequence can vary from that shown in SEQ ID NO:1 and still encode a TRAIL-R protein having the amino acid sequence of SEQ ID NO:2. Such variant DNA sequences may result from silent mutations (e.g., occurring during PCR amplification), or may be the product of deliberate mutagenesis of a native sequence. Thus, among the DNA sequences provided herein are native TRAIL-R sequences (e.g., cDNA comprising the nucleotide sequence presented in SEQ ID NO:1) and DNA that is degenerate as a result of the genetic code to a native TRAIL-R DNA sequence.

Among the TRAIL-R polypeptides provided herein are variants of native TRAIL-R polypeptides that retain a biological activity of a native TRAIL-R. Such variants include polypeptides that are substantially homologous to native TRAIL-R, but which have an amino acid sequence different from that of a native TRAIL-R because of one or more deletions, insertions or substitutions. Particular embodiments include, but are not limited to, TRAIL-R polypeptides that comprise from one to ten deletions, insertions or substitutions of amino acid residues, when compared to a native TRAIL-R sequence. The TRAIL-R-encoding DNAs of the present invention include variants that differ from a native TRAIL-R DNA sequence because of one or more deletions, insertions or substitutions, but that encode a biologically active TRAIL-R polypeptide. One biological activity of TRAIL-R is the ability to bind TRAIL.

Nucleic acid molecules capable of hybridizing to the DNA of SEQ ID NO:1 or SEQ ID NO:3 under moderately stringent or highly stringent conditions, and which encode a biologically active TRAIL-R, are provided herein. Such hybridizing nucleic acids include, but are not limited to, variant DNA sequences and DNA derived from non-human species, e.g., non-human mammals.

Moderately stringent conditions include conditions described in, for example, Sambrook et al, *Molecular Cloning: A Laboratory Manual,* 2nd ed., Vol. 1, pp 1.101–104, Cold Spring Harbor Laboratory Press, 1989. Conditions of moderate stringency, as defined by Sambrook et al., include use of a prewashing solution of 5×SSC, 0.5% SDS, 1.0 mM EDTA (pH 8.0) and hybridization conditions of about 55° C., 5×SSC, overnight. Highly stringent conditions include higher temperatures of hybridization and washing. One embodiment of the invention is directed to DNA sequences that will hybridize to the DNA of SEQ ID NOS:1 or 3 under highly stringent conditions, wherein said conditions include hybridization at 68° C. followed by washing in 0.1×SSC/0.1% SDS at 63–68° C.

Certain DNAs and polypeptides provided herein comprise nucleotide or amino acid sequences, respectively, that are at least 80% identical to a native TRAIL-R sequence. Also contemplated are embodiments in which a TRAIL-R DNA or polypeptide comprises a sequence that is at least 90% identical, at least 95% identical, or at least 98% identical to a native TRAIL-R sequence. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

In particular embodiments of the invention, a variant TRAIL-R polypeptide differs in amino acid sequence from a native TRAIL-R, but is substantially equivalent to a native TRAIL-R in a biological activity. One example is a variant TRAIL-R that binds TRAIL with essentially the same binding affinity as does a native TRAIL-R. Binding affinity can be measured by conventional procedures, e.g., as described in U.S. Pat. No. 5,512,457.

Variant amino acid sequences may comprise conservative substitution(s), meaning that one or more amino acid residues of a native TRAIL-R is replaced by a different residue, but that the conservatively substituted TRAIL-R polypeptide retains a desired biological activity of the native protein (e.g., the ability to bind TRAIL). A given amino acid may be replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other conservative substitutions, e.g., involving substitutions of entire regions having similar hydrophobicity characteristics, are well known.

In another example of variants, sequences encoding Cys residues that are not essential for biological activity can be altered to cause the Cys residues to be deleted or replaced with other amino acids, preventing formation of incorrect intramolecular disulfide bridges upon renaturation. Certain receptors of the TNF-R family contain cysteine-rich repeat motifs in their extracellular domains (Marsters et al., *J. Biol. Chem.* 267:5747–5750, 1992). These repeats are believed to be important for ligand binding. To illustrate, Marsters et al., supra, reported that soluble TNF-R type 1 polypeptides lacking one of the repeats exhibited a ten fold reduction in binding affinity for TNFα and TNFβ; deletion of the second repeat resulted in a complete loss of detectable binding of the ligands. The human TRAIL-R of SEQ ID NO:2 contains two such cysteine rich repeats, the first including residues 94 through 137, and the second including residues 138 through 178. Cysteine residues within these cysteine rich domains advantageously remain unaltered in TRAIL-R variants, when retention of TRAIL-binding activity is desired.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Mature human TRAIL-R contains such adjacent basic residue pairs at amino acids 72–73, 154–155, 322–323, 323–324, and 359–360 of SEQ ID NO:2. Lys-Lys pairings are considerably less susceptible to KEX2 cleavage, and conversion of Arg-Lys or Lys-Arg to Lys-Lys represents a conservative and preferred approach to inactivating KEX2 sites.

TRAIL-R polypeptides, including variants and fragments thereof, can be tested for biological activity in any suitable assay. The ability of a TRAIL-R polypeptide to bind TRAIL can be confirmed in conventional binding assays, examples of which are described below.

Expression Systems

The present invention also provides recombinant cloning and expression vectors containing TRAIL-R DNA, as well as host cell containing the recombinant vectors. Expression vectors comprising TRAIL-R DNA may be used to prepare TRAIL-R polypeptides encoded by the DNA. A method for producing TRAIL-R polypeptides comprises culturing host cells transformed with a recombinant expression vector encoding TRAIL-R, under conditions that promote expression of TRAIL-R, then recovering the expressed TRAIL-R polypeptides from the culture. The skilled artisan will recognize that the procedure for purifying the expressed TRAIL-R will vary according to such factors as the type of host cells employed, and whether the TRAIL-R is membrane-bound or a soluble form that is secreted from the host cell.

Any suitable expression system may be employed. The vectors include a DNA encoding a TRAIL-R polypeptide, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the TRAIL-R DNA sequence. Thus, a promoter nucleotide sequence is operably linked to an TRAIL-R DNA sequence if the promoter nucleotide sequence controls the transcription of the TRAIL-R DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the TRAIL-R sequence so that the TRAIL-R is initially translated as a fusion protein comprising the signal peptide. A signal peptide that is functional in the intended host cells promotes extracellular secretion of the TRAIL-R polypeptide. The signal peptide is cleaved from the TRAIL-R polypeptide upon secretion of TRAIL-R from the cell.

Suitable host cells for expression of TRAIL-R polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce TRAIL-R polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a TRAIL-R polypeptide may include an N-terminal methionine residue to facilitate expression of the recombinant polypeptide in the prokaryotic host cell. The N-terminal Met may be cleaved from the expressed recombinant TRAIL-R polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a TRAIL-R DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9, ATCC 37092) and pPLc28 (resident in *E. coli* RR1, ATCC 53082).

TRAIL-R alternatively may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the TRAIL polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Mammalian or insect host cell culture systems also may be employed to express recombinant TRAIL-R polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Expression vectors for use in mammalian host cells can be constructed as disclosed by Okayama and Berg (*Mol. Cell. Biol.* 3:280, 1983), for example. A useful system for stable high level expression of mammalian cDNAs in C127 murine mammary epithelial cells can be constructed substantially as described by Cosman et al. (*Mol. Immunol.* 23:935, 1986). A high expression vector, PMLSV N1/N4, described by Cosman et al., *Nature* 312:768, 1984 has been deposited as ATCC 39890. Additional mammalian expression vectors are described in EP-A-0367566, and in WO 91/18982. As one alternative, the vector may be derived from a retrovirus.

Overexpression of full length TRAIL-R has resulted in membrane blebbing and nuclear condensation of transfected CV-1/EBNA cells, indicating that the mechanism of cell death was apoptosis. For host cells in which such TRAIL-R-mediated apoptosis occurs, a suitable apoptosis inhibitor may be included in the expression system.

To inhibit TRAIL-R-induced apoptosis of host cells expressing recombinant TRAIL-R, the cells may be co-transfected with an expression vector encoding a polypeptide that functions as an apoptosis inhibitor. Expression vectors encoding such polypeptides can be prepared by conventional procedures. Another approach involves adding an apoptosis inhibitor to the culture medium. The use of poxvirus CrmA, baculovirus P35, a C-terminal fragment of FADD, and the tripeptide derivative zVAD-fmk, to reduce death of host cells is illustrated in examples 6 and 8.

zVAD-fmk (benzyloxycarbonyl-Val-Ala-Asp-fluoromethylketone) is a tripeptide based compound, available from Enzyme System Products, Dublin, Calif. As illustrated in example 8, zVAD-fmk may be added to the medium in which cells expressing TRAIL-R are cultured.

The 38-kilodalton cowpox-derived protein that was subsequently designated CrmA is described in Pickup et al. (*Proc. Natl. Acad. Sci. USA* 83:7698–7702, 1986; hereby incorporated by reference). Sequence information for CrmA is presented in FIG. 4 of Pickup et al., supra. One approach to producing and purifying CrmA protein is described in Ray et al. (*Cell,* 69:597–604, 1992; hereby incorporated by reference).

A 35-kilodalton protein encoded by *Autographa californica* nuclear polyhedrosis virus, a baculovirus, is described in Friesen and Miller (*J. Virol.* 61:2264–2272, 1987; hereby incorporated by reference). Sequence information for this protein, designated baculovirus p35 herein, is presented in FIG. 5 of Friesen and Miller, supra.

The death domain-containing cytoplasmic protein FADD (also known as MORT1) is described in Boldin et al. (*J. Biol. Chem.* 270:7795–7798, 1995; hereby incorporated by reference). FADD has been reported to associate, directly or indirectly, with the cytoplasmic death domain of certain receptors that mediate apoptosis (Boldin et al., *Cell* 85:803–815, June 1996; Hsu et al., *Cell* 84:299–308, January 1996).

In one embodiment of the present invention, truncated FADD polypeptides that include the death domain (located in the C-terminal portion of the protein), but lack the N-terminal region to which apoptosis effector functions have been attributed, are employed to reduce apoptosis. The use of certain FADD deletion mutant polypeptides, truncated at the N-terminus, to inhibit death of cells expressing other apoptosis-inducing receptors, is described in Hsu et al. (*Cell* 84:299–308, 1996; hereby incorporated by reference).

This approach is illustrated in example 8, which employs one suitable FADD-dominant negative (FADD-DN) polypeptide, having an amino acid sequence corresponding to amino acids 117 through 245 of the MORT1 amino acid sequence presented in Boldin et al. (*J. Biol. Chem.* 270:7795–7798, 1995). In example 8, cells were co-transfected with a TRAIL-R-encoding expression vector, and with an expression vector encoding the above-described Flag® peptide, fused to the N-terminus of the FADD-DN polypeptide.

While not wishing to be bound by theory, one possible explanation is that the C-terminal fragments of FADD associate with the intracellular death domain of the receptor, but lack the N-terminal portion of the protein that is necessary for effecting apoptosis (Hsu et al., *Cell* 84:299–308, January 1996; Boldin et al., *Cell* 85:803–815, June 1996). The truncated FADD thereby may block association of endogenous, full length FADD with the receptor's death domain; consequently, the apoptosis that would be initiated by such endogenous FADD is inhibited.

Other apoptosis inhibitors useful in expression systems of the present invention can be identified in conventional assay procedures. One such assay, in which compounds are tested for the ability to reduce apoptosis of cells expressing TRAIL-R, is described in example 8.

Poxvirus CrmA, baculovirus P35, and zVAD-fmk are viral caspase inhibitors. Other caspase inhibitors may be tested for the ability to reduce TRAIL-R-mediated cell death.

The use of CrmA, baculovirus p35, and certain peptide derivatives (including zVAD-fmk) as inhibitors of apoptosis in particular cells/systems is discussed in Sarin et al. (*J. Exp. Med.* 184:2445–2450, December 1996; hereby incorporated by reference). The role of interleukin-1β converting enzyme (ICE) family proteases in signal transduction cascades leading to programmed cell death, and the use of inhibitors of such proteases to block apoptosis, is discussed in Sarin et al., supra, and Muzio et al., *Cell* 85:817–827, 1996).

Apoptosis inhibitors generally need not be employed for expression of TRAIL-R polypeptides lacking the cytoplasmic domain (i.e., lacking the region of the protein involved in signal transduction). Thus, expression systems for producing soluble TRAIL-R polypeptides comprising only the extracellular domain (or a fragment thereof) need not include one of the above-described apoptosis inhibitors.

Regarding signal peptides that may be employed in producing TRAIL-R, the native signal peptide of TRAIL-R may be replaced by a heterologous signal peptide or leader sequence, if desired. The choice of signal peptide or leader may depend on factors such as the type of host cells in which the recombinant TRAIL-R is to be produced. To illustrate, examples of heterologous signal peptides that are functional in mammalian host cells include the signal sequence for interleukin-7 (IL-7) described in U.S. Pat. 4,965,195, the signal sequence for interleukin-2 receptor described in Cosman et al., *Nature* 312:768 (1984); the interleukin4 receptor signal peptide described in EP 367,566; the type I interleukin-1 receptor signal peptide described in U.S. Pat. 4,968,607; and the type II interleukin-1 receptor signal peptide described in EP 460,846.

Oligomeric Forms of TRAIL-R

Encompassed by the present invention are oligomers that contain TRAIL-R polypeptides. TRAIL-R oligomers may be in the form of covalently-linked or non-covalently-linked dimers, trimers, or higher oligomers.

One embodiment of the invention is directed to oligomers comprising multiple TRAIL-R polypeptides joined via covalent or non-covalent interactions between peptide moieties fused to the TRAIL-R polypeptides. Such peptides may be peptide linkers (spacers), or peptides that have the property of promoting oligomerization. Leucine zippers and certain polypeptides derived from antibodies are among the peptides that can promote oligomerization of TRAIL-R polypeptides attached thereto, as described in more detail below.

In particular embodiments, the oligomers comprise from two to four TRAIL-R polypeptides. The TRAIL-R moieties of the oligomer may be soluble polypeptides, as described above.

As one alternative, a TRAIL-R oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1–10.19.11, 1992).

One embodiment of the present invention is directed to a TRAIL-R dimer comprising two fusion proteins created by fusing TRAIL-R to the Fc region of an antibody. A gene fusion encoding the TRAIL-R/Fc fusion protein is inserted into an appropriate expression vector. TRAIL-R/Fc fusion proteins are expressed in host cells transformed with the recombinant expression vector, and allowed to assemble much like antibody molecules, whereupon interchain disulfide bonds form between the Fc moieties to yield divalent TRAIL-R.

Provided herein are fusion proteins comprising a TRAIL-R polypeptide fused to an Fc polypeptide derived from an antibody. DNA encoding such fusion proteins, as well as dimers containing two fusion proteins joined via disulfide bonds between the Fc moieties thereof, are also provided. The term "Fc polypeptide" as used herein includes native and mutein forms of polypeptides derived from the Fc region of an antibody. Truncated forms of such polypeptides containing the hinge region that promotes dimerization are also included.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992–4001, 1994). The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, TRAIL-R may be substituted for the variable portion of an antibody heavy or light chain. If fusion proteins are made with both heavy and light chains of an antibody, it is possible to form a TRAIL-R oligomer with as many as four TRAIL-R extracellular regions.

Alternatively, the oligomer is a fusion protein comprising multiple TRAIL-R polypeptides, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences encoding TRAIL-R, using any suitable conventional technique. For example, a chemically synthesized oligonucleotide encoding the linker may be ligated between sequences encoding TRAIL-R. In particular embodiments, a fusion protein comprises from two to four soluble TRAIL-R polypeptides, separated by peptide linkers.

Another method for preparing oligomeric TRAIL-R involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

Examples of leucine zipper domains suitable for producing soluble oligomeric proteins are described in PCT application WO 94/10308, and the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267–278, 1994). Recombinant fusion proteins comprising a soluble TRAIL-R polypeptide fused to a leucine zipper peptide are expressed in suitable host cells, and the soluble oligomeric TRAIL-R that forms is recovered from the culture supernatant.

Oligomeric TRAIL-R has the property of bivalent, trivalent, etc. binding sites for TRAIL. The above-described fusion proteins comprising Fc moieties (and oligomers formed therefrom) offer the advantage of facile purification by affinity chromatography over Protein A or Protein G columns. DNA sequences encoding oligomeric TRAIL-R, or encoding fusion proteins useful in preparing TRAIL-R oligomers, are provided herein.

Assays

TRAIL-R proteins (including fragments, variants, oligomers, and other forms of TRAIL-R) may be tested for the ability to bind TRAIL in any suitable assay, such as a conventional binding assay. To illustrate, TRAIL-R may be labeled with a detectable reagent (e.g., a radionuclide, chromophore, enzyme that catalyzes a colorimetric or fluorometric reaction, and the like). The labeled TRAIL-R is contacted with cells expressing TRAIL. The cells then are washed to remove unbound labeled TRAIL-R, and the presence of cell-bound label is determined by a suitable technique, chosen according to the nature of the label.

One example of a binding assay procedure is as follows. A recombinant expression vector containing TRAIL cDNA is constructed, e.g., as described in in PCT application WO 97/01633, hereby incorporated by reference. DNA and amino acid sequence information for human and mouse TRAIL is presented in WO 97/01633. TRAIL comprises an N-terminal cytoplasmic domain, a transmembrane region, and a C-terminal extracellular domain. CV1-EBNA-1 cells in 10 $cm^2$ dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

The transfected cells are cultured for 24 hours, and the cells in each dish then are split into a 24-well plate. After culturing an additional 48 hours, the transfected cells (about $4 \times 10^4$ cells/well) are washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of a soluble TRAIL-R/Fc fusion protein. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any TRAIL-R/Fc protein that has bound to the cells. In all assays, non-specific binding of $^{125}$I-antibody is assayed in the absence of TRAIL-R/Fc, as well as in the presence of TRAIL-R/Fc and a 200-fold molar excess of unlabeled mouse anti-human IgG antibody.

Cell-bound $^{125}$I-antibody is quantified on a Packard Autogamma counter. Affinity calculations (Scatchard, *Ann. N.Y. Acad. Sci.* 51:660, 1949) are generated on RS/1 (BBN Software, Boston, Mass.) run on a Microvax computer.

Another type of suitable binding assay is a competitive binding assay. To illustrate, biological activity of a TRAIL-R variant may be determined by assaying for the variant's ability to compete with a native TRAIL-R for binding to TRAIL.

Competitive binding assays can be performed by conventional methodology. Reagents that may be employed in competitive binding assays include radiolabeled TRAIL-R and intact cells expressing TRAIL (endogenous or recombinant) on the cell surface. For example, a radiolabeled soluble TRAIL-R fragment can be used to compete with a soluble TRAIL-R variant for binding to cell surface TRAIL. Instead of intact cells, one could substitute a soluble TRAIL/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J. Another type of competitive binding assay utilizes radiolabeled soluble TRAIL, such as a soluble TRAIL/Fc fusion protein, and intact cells expressing TRAIL-R. Qualitative results can be obtained by competitive autoradiographic plate binding assays, while Scatchard plots (Scatchard, *Ann. N.Y. Acad. Sci.* 51:660, 1949) may be utilized to generate quantitative results.

Another type of assay for biological activity involves testing a TRAIL-R polypeptide for the ability to block TRAIL-mediated apoptosis of target cells, such as the human leukemic T-cell line known as Jurkat cells, for example. TRAIL-mediated apoptosis of the cell line designated Jurkat clone E6-1 (ATCC TIB 152) is demonstrated in assay procedures described in PCT application WO 97/01633, hereby incorporated by reference.

Uses of TRAIL-R

Uses of TRAIL-R include, but are not limited to, the following. Certain of these uses of TRAIL-R flow from its ability to bind TRAIL.

TRAIL-R finds use as a protein purification reagent. TRAIL-R polypeptides may be attached to a solid support material and used to purify TRAIL proteins by affinity chromatography. In particular embodiments, a TRAIL-R polypeptide (in any form described herein that is capable of binding TRAIL) is attached to a solid support by conventional procedures. As one example, chromatography columns containing functional groups that will react with functional groups on amino acid side chains of proteins are available (Pharmacia Biotech, Inc., Piscataway, N.J.). In an alternative, a TRAIL-R/Fc protein is attached to Protein A- or Protein G-containing chromatography columns through interaction with the Fc moiety.

TRAIL-R proteins also find use in measuring the biological activity of TRAIL proteins in terms of their binding affinity for TRAIL-R. TRAIL-R proteins thus may be employed by those conducting "quality assurance" studies, e.g., to monitor shelf life and stability of TRAIL protein under different conditions. To illustrate, TRAIL-R may be employed in a binding affinity study to measure the biological activity of a TRAIL protein that has been stored at different temperatures, or produced in different cell types. TRAIL-R also may be used to determine whether biological activity is retained after modification of a TRAIL protein (e.g., chemical modification, truncation, mutation, etc.). The binding affinity of the modified TRAIL protein for TRAIL-R is compared to that of an unmodified TRAIL protein to detect any adverse impact of the modifications on biological activity of TRAIL. The biological activity of a TRAIL protein thus can be ascertained before it is used in a research study, for example.

TRAIL-R also finds use in purifying or identifying cells that express TRAIL on the cell surface. TRAIL-R polypeptides are bound to a solid phase such as a column chromatography matrix or a similar suitable substrate. For example, magnetic microspheres can be coated with TRAIL-R and held in an incubation vessel through a magnetic field. Suspensions of cell mixtures containing TRAIL-expressing cells are contacted with the solid phase having TRAIL-R thereon. Cells expressing TRAIL on the cell surface bind to the fixed TRAIL-R, and unbound cells then are washed away.

Alternatively, TRAIL-R can be conjugated to a detectable moiety, then incubated with cells to be tested for TRAIL expression. After incubation, unbound labeled TRAIL-R is removed and the presence or absence of the detectable moiety on the cells is determined.

In a further alternative, mixtures of cells suspected of containing TRAIL$^+$ cells are incubated with biotinylated TRAIL-R. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (see Berenson, et al. *J. Cell. Biochem.,* 10D:239, 1986). Washing to remove unbound material, and the release of the bound cells, are performed using conventional methods.

TRAIL-R polypeptides also find use as carriers for delivering agents attached thereto to cells bearing TRAIL. Cells expressing TRAIL include those identified in Wiley et al. (*Immunity,* 3:673–682, 1995). TRAIL-R proteins thus can be used to deliver diagnostic or therapeutic agents to such cells (or to other cell types found to express TRAIL on the cell surface) in in vitro or in vivo procedures.

Detectable (diagnostic) and therapeutic agents that may be attached to a TRAIL-R polypeptide include, but are not limited to, toxins, other cytotoxic agents, drugs, radionuclides, chromophores, enzymes that catalyze a calorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu.

Such agents may be attached to the TRAIL-R by any suitable conventional procedure. TRAIL-R, being a protein, comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.) A number of techniques for radiolabeling proteins are known. Radionuclide metals may be attached to TRAIL-R by using a suitable bifunctional chelating agent, for example.

Conjugates comprising TRIAL-R and a suitable diagnostic or therapeutic agent (preferably covalently linked) are thus prepared. The conjugates are administered or otherwise employed in an amount appropriate for the particular application.

TRIAL-R DNA and polypeptides of the present invention may be used in developing treatments for any disorder mediated (directly or indirectly) by defective, or insufficient amounts of, TRIAL-R. TRIAL-R polypeptides may be administered to a mammal afflicted with such a disorder. Alternatively, a gene therapy approach may be taken. Disclosure herein of native TRAIL-R nucleotide sequences permits the detection of defection TRIAL-R genes, and the replacement thereof with normal TRIAL-R-encoding genes. Defective genes mat be detected in in vitro diagnostic assays, and by comparision of a native TRAIL-R nucleotide sequence disclosed herein with that of a TRAIL-R gene derived from a person suspected of harboring a defect in this gene.

Another use of the protein of the present invention is as a research tool for studying the biological effects that result from inhibiting TRAIL/TRAIL-R interactions on different cell types. TRAIL-R polypeptides also may be employed in in vitro assays for detecting TRAIL or TRAIL-R or the interactions thereof.

TRAIL-R may be employed in inhibiting a biological activity of TRAIL, in in vitro or in vivo procedures. A purified TRAIL-R polypeptide may be used to inhibit binding of TRAIL to endogenous cell surface TRAIL-R. Biological effects that result from the binding of TRAIL to endogenous receptors thus are inhibited. Various forms of TRAIL-R may be employed, including, for example, the above-described TRAIL-R fragments, oligomers, derivatives, and variants that are capable of binding TRAIL. In one embodiment, a soluble TRAIL-R is employed to inhibit a biological activity of TRAIL, e.g., to inhibit TRAIL-mediated apoptosis of particular cells.

TRAIL-R may be administered to a mammal to treat a TRAIL-mediated disorder. Such TRAIL-mediated disorders include conditions caused (directly or indirectly) or exacerbated by TRAIL.

TRAIL-R may be useful for treating thrombotic microangiopathies. One such disorder is thrombotic thrombocytopenic purpura (TTP) (Kwaan, H. C., *Semin. Hematol.,* 24:71, 1987; Thompson et al., *Blood,* 80:1890, 1992). Increasing TTP-associated mortality rates have been reported by the U.S. Centers for Disease Control (Torok et al., *Am. J. Hematol.* 50:84, 1995).

Plasma from patients afflicted with TTP (including $HIV^+$ and $HIV^-$ patients) induces apoptosis of human endothelial cells of dermal microvascular origin, but not large vessel origin (Laurence et al., *Blood,* 87:3245, Apr. 15, 1996). Plasma of TTP patients thus is thought to contain one or more factors that directly or indirectly induce apoptosis. As described in PCT application WO 97/01633 (hereby incorporated by reference), TRAIL is present in the serum of TTP patients, and may play a role in inducing apoptosis of microvascular endothelial cells.

Another thrombotic microangiopathy is hemolytic-uremic syndrome (HUS) (Moake, J. L., *Lancet,* 343:393, 1994; Melnyk et al., (*Arch. Intern. Med.,* 155:2077, 1995; Thompson et al., supra). One embodiment of the invention is directed to use of TRAIL-R to treat the condition that is often referred to as "adult HUS" (even though it can strike children as well). A disorder known as childhood/diarrhea-associated HUS differs in etiology from adult HUS.

Other conditions characterized by clotting of small blood vessels may be treated using TRAIL-R. Such conditions include but are not limited to the following. Cardiac problems seen in about 5–10% of pediatric AIDS patients are believed to involve clotting of small blood vessels. Breakdown of the microvasculature in the heart has been reported in multiple sclerosis patients. As a further example, treatment of systemic lupus erythematosus (SLE) is contemplated.

In one embodiment, a patient's blood or plasma is contacted with TRAIL-R ex vivo. The TRAIL-R may be bound to a suitable chromatography matrix by conventional procedures. The patient's blood or plasma flows through a chromatography column containing TRAIL-R bound to the matrix, before being returned to the patient. The immobilized receptor binds TRAIL, thus removing TRAIL protein from the patient's blood.

Alternatively, TRAIL-R may be administered in vivo to a patient afflicted with a thrombotic microangiopathy. In one embodiment, a soluble form of TRAIL-R is administered to the patient.

The present invention thus provides a method for treating a thrombotic microangiopathy, involving use of an effective amount of TRAIL-R. A TRAIL-R polypeptide may be employed in in vivo or ex vivo procedures, to inhibit TRAIL-mediated damage to (e.g., apoptosis of) microvascular endothelial cells.

TRAIL-R may be employed in conjunction with other agents useful in treating a particular disorder. In an in vitro study reported by Laurence et al. (*Blood* 87:325, 1996), some reduction of TTP plasma-mediated apoptosis of microvascular endothelial cells was achieved by using an anti-Fas blocking antibody, aurintricarboxylic acid, or normal plasma depleted of cryoprecipitate.

Thus, a patient may be treated with an agent that inhibits Fas-ligand-mediated apoptosis of endothelial cells, in combination with an agent that inhibits TRAIL-mediated apoptosis of endothelial cells. In one embodiment, TRAIL-R and an anti-FAS blocking antibody are both administered to a patient afflicted with a disorder characterized by thrombotic microangiopathy, such as TTP or HUS. Examples of blocking monoclonal antibodies directed against Fas antigen (CD95) are described in PCT application publication number WO 95/10540, hereby incorporated by reference.

Another embodiment of the present invention is directed to the use of TRAIL-R to reduce TRAIL-mediated death of T cells in HIV-infected patients. The role of T cell apoptosis in the development of AIDS has been the subject of a number of studies (see, for example, Meyaard et al., *Science* 257:217–219, 1992; Groux et al., *J Exp. Med.,* 175:331, 1992; and Oyaizu et al., in *Cell Activation and Apoptosis in HIV Infection,* Andrieu and Lu, Eds., Plenum Press, New York, 1995, pp. 101–114). Certain investigators have studied the role of Fas-mediated apoptosis; the involvement of interleukin-1β-converting enzyme (ICE) also has been explored (Estaquier et al., *Blood* 87:4959–4966, 1996; Mitra et al., *Immunology* 87:581–585, 1996; Katsikis et al., *J. Exp. Med.* 181:2029–2036, 1995). It is possible that T cell apoptosis occurs through multiple mechanisms.

At least some of the T cell death seen in $HIV^+$ patients is believed to be mediated by TRAIL. While not wishing to be bound by theory, such TRAIL-mediated T cell death is believed to occur through the mechanism known as activation-induced cell death (AICD).

Activated human T cells are induced to undergo programmed cell death (apoptosis) upon triggering through the CD3/T cell receptor complex, a process termed activated-induced cell death (AICD). AICD of $CD4^+$ T cells isolated from HIV-infected asymptomatic individuals has been reported (Groux et al., supra). Thus, AICD may play a role in the depletion of $CD4^+$ T cells and the progression to AIDS in HIV-infected individuals.

The present invention provides a method of inhibiting TRAIL-mediated T cell death in $HIV^+$ patients, comprising administering TRAIL-R (preferably, a soluble TRAIL-R polypeptide) to the patients. In one embodiment, the patient is asymptomatic when treatment with TRAIL-R commences. If desired, prior to treatment, peripheral blood T cells may be extracted from an HIV+ patient, and tested for susceptibility to TRAIL-mediated cell death by conventional procedures.

In one embodiment, a patient's blood or plasma is contacted with TRAIL-R ex vivo. The TRAIL-R may be bound to a suitable chromatography matrix by conventional procedures. The patient's blood or plasma flows through a chromatography column containing TRAIL-R bound to the matrix, before being returned to the patient. The immobilized TRAIL-R binds TRAIL, thus removing TRAIL protein from the patient's blood.

In treating HIV+ patients, TRAIL-R may be employed in combination with other inhibitors of T cell apoptosis. Fas-mediated apoptosis also has been implicated in loss of T cells in HIV+ individuals (Katsikis et al., *J. Exp. Med.* 181:2029–2036, 1995). Thus, a patient susceptible to both Fas ligand (Fas-L)-mediated and TRAIL-mediated T cell death may be treated with both an agent that blocks TRAIL/TRAIL-R interactions and an agent that blocks Fas-L/Fas interactions. Suitable agents for blocking binding of Fas-L to Fas include, but are not limited to, soluble Fas polypeptides; oligomeric forms of soluble Fas polypeptides (e.g., dimers of sFas/Fc); anti-Fas antibodies that bind Fas without transducing the biological signal that results in apoptosis; anti-Fas-L antibodies that block binding of Fas-L to Fas; and muteins of Fas-L that bind Fas but don't transduce the biological signal that results in apoptosis. Preferably, the antibodies employed in the method are monoclonal antibodies. Examples of suitable agents for blocking Fas-L/Fas interactions, including blocking anti-Fas monoclonal antibodies, are described in WO 95/10540, hereby incorporated by reference.

Compositions comprising an effective amount of a TRAIL-R polypeptide of the present invention, in combination with other components such as a physiologically acceptable diluent, carrier, or excipient, are provided herein. TRAIL-R can be formulated according to known methods used to prepare pharmaceutically useful compositions. TRAIL-R can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa.

In addition, such compositions can contain TRAIL-R complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of TRAIL-R, and are thus chosen according to the intended application. TRAIL-R expressed on the surface of a cell may find use, as well.

Compositions of the present invention may contain a TRAIL-R polypeptide in any form described herein, such as native proteins, variants, derivatives, oligomers, and biologically active fragments. In particular embodiments, the composition comprises a soluble TRAIL-R polypeptide or an oligomer comprising soluble TRAIL-R polypeptides.

TRAIL-R can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration.

Preliminary doses can be determined according to animal tests, and the scaling of dosages for human administration are performed according to art-accepted practices.

Compositions comprising TRAIL-R nucleic acids in physiologically acceptable formulations are also contemplated. TRAIL-R DNA may be formulated for injection, for example.

Antibodies

Antibodies that are immunoreactive with TRAIL-R polypeptides are provided herein. Such antibodies specifically bind TRAIL-R, in that the antibodies bind to TRAIL-R via the antigen-binding sites of the antibody (as opposed to non-specific binding).

The TRAIL-R protein prepared as described in example 1 may be employed as an immunogen in producing antibodies immunoreactive therewith. Alternatively, another form of TRAIL-R, such as a fragment or fusion protein, is employed as the immunogen.

Polyclonal and monoclonal antibodies may be prepared by conventional techniques. See, for example, *Monoclonal Antibodies, Hybridomas: A New Dimension in Biological Analyses,* Kennet et al. (eds.), Plenum Press, New York (1980); and *Antibodies: A Laboratory Manual,* Harlow and Land (eds.), Cold Spring Harbor Laboratory Press, Cold Spring Harbor, N.Y., (1988). Production of monoclonal antibodies directed against TRAIL-R is further illustrated in example 4.

Antigen-binding fragments of such antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993).

Among the uses of the antibodies is use in assays to detect the presence of TRAIL-R polypeptides, either in vitro or in vivo. The antibodies also may be employed in purifying TRAIL-R proteins by immunoaffinity chromatography.

Those antibodies that additionally can block binding of TRAIL-R to TRAIL may be used to inhibit a biological activity that results from such binding. Such blocking antibodies may be identified using any suitable assay procedure, such as by testing antibodies for the ability to inhibit binding of TRAIL to cells expressing TRAIL-R. Examples of such cells are the Jurkat cells and PS 1 cells described in example 2 below. Alternatively, blocking antibodies may be identified in assays for the ability to inhibit a biological effect that results from binding of TRAIL to target cells. Antibodies may be assayed for the ability to inhibit TRAIL-mediated lysis of Jurkat cells, for example.

Such an antibody may be employed in an in vitro procedure, or administered in vivo to inhibit a TRAIL-R-mediated biological activity. Disorders caused or exacerbated (directly or indirectly) by the interaction of TRAIL with cell surface TRAIL receptor thus may be treated. A therapeutic method involves in vivo administration of a blocking antibody to a mammal in an amount effective in inhibiting a TRAIL-mediated biological activity. Disorders caused or exacerbated by TRAIL, directly or indirectly, are thus treated. Monoclonal antibodies are generally preferred for use in such therapeutic methods. In one embodiment, an antigen-binding antibody fragment is employed.

A blocking antibody directed against TRAIL-R may be substituted for TRAIL-R in the above-described method of treating thrombotic microangiopathy, e.g., in treating TTP or HUS. The antibody is administered in vivo, to inhibit TRAIL-mediated damage to (e.g., apoptosis of) microvascular endothelial cells.

Antibodies raised against TRAIL-R may be screened for agonistic (i.e., ligand-mimicking) properties. Such antibodies, upon binding to cell surface TRAIL-R, induce biological effects (e.g., transduction of biological signals) similar to the biological effects induced when TRAIL binds to cell surface TRAIL-R. Agonistic antibodies may be used to induce apoptosis of certain cancer cells or virally infected cells, as has been reported for TRAIL. The ability of TRAIL to kill cancer cells (including but not limited to leukemia, lymphoma, and melanoma cells) and virally infected cells is described in Wiley et al. (*Immunity* 3:673–682, 1995); and in PCT application WO 97/01633.

Compositions comprising an antibody that is directed against TRAIL-R, and a physiologically acceptable diluent, excipient, or carrier, are provided herein. Suitable components of such compositions are as described above for compositions containing TRAIL-R proteins.

Also provided herein are conjugates comprising a detectable (e.g., diagnostic) or therapeutic agent, attached to an antibody directed against TRAIL-R. Examples of such agents are presented above. The conjugates find use in in vitro or in vivo procedures.

Nucleic Acids

The present invention provides TRAIL-R nucleic acids. Such nucleic acids include, but are not limited to, DNA encoding the peptide described in example 2. Such DNAs can be identified from knowledge of the genetic code. Other nucleic acids of the present invention include isolated DNAs comprising the nucleotide sequence presented in SEQ ID NO:1 or SEQ ID NO:3.

The present invention provides isolated nucleic acids useful in the production of TRAIL-R polypeptides, e.g., in the recombinant expression systems discussed above. Such nucleic acids include, but are not limited to, the human TRAIL-R DNA of SEQ ID NO:1. Nucleic acid molecules of the present invention include TRAIL-R DNA in both single-stranded and double-stranded form, as well as the RNA complement thereof. TRAIL-R DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO:1 or 3, or a suitable fragment thereof, as a probe.

DNAs encoding TRAIL-R in any of the forms contemplated herein (e.g., full length TRAIL-R or fragments thereof) are provided. Particular embodiments of TRAIL-R-encoding DNAs include a DNA encoding the full length human TRAIL-R of SEQ ID NO:2 (including the N-terminal signal peptide), and a DNA encoding a full length mature human TRAIL-R. Other embodiments include DNA encoding a soluble TRAIL-R (e.g., encoding the extracellular domain of the protein of SEQ ID NO:2, either with or without the signal peptide).

One embodiment of the invention is directed to fragments of TRAIL-R nucleotide sequences comprising at least about 17 contiguous nucleotides of a TRAIL-R DNA sequence. In other embodiments, a DNA fragment comprises at least 30, or at least 60, contiguous nucleotides of a TRAIL-R DNA sequence. Nucleic acids provided herein include DNA and RNA complements of said fragments, along with both single-stranded and double-stranded forms of the TRAIL-R DNA.

Among the uses of TRAIL-R nucleic acid fragments is use as probes or primers. Using knowledge of the genetic code in combination with the amino acid sequences set forth in example 2, sets of degenerate oligonucleotides can be prepared. Such oligonucleotides find use as primers, e.g., in polymerase chain reactions (PCR), whereby TRAIL-R DNA fragments are isolated and amplified.

Other useful fragments of the TRAIL-R nucleic acids include antisense or sense oligonucleotides comprising a single-stranded nucleic acid sequence (either RNA or DNA) capable of binding to target TRAIL-R mRNA (sense) or TRAIL-R DNA (antisense) sequences. Antisense or sense oligonucleotides, according to the present invention, comprise a fragment of the coding region of TRAIL-R DNA. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes. premature termination of transcription or translation, or by other means. The antisense oligonucleotides thus may be used to block expression of TRAIL-R proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are provided to further illustrate particular embodiments of the invention, and are not to be construed as limiting the scope of the present invention.

EXAMPLE 1

Purification of TRAIL-R Protein

A human TRAIL receptor (TRAIL-R) protein was prepared by the following procedure. Trail-R was isolated from the cell membranes of Jurkat cells, a human acute T leukemia cell line. Jurkat cells were chosen because a specific band can be affinity precipitated from surface-biotinylated Jurkat cells, using Flag®-TRAIL covalently coupled to affi-gel beads (Biorad Laboratories, Richmond, Calif.). The precipitated band has a molecular weight of about 52 kD. A minor specific band of about 42 kD also was present, possibly accounting for a proteolytic breakdown product or a less glycosylated form of TRAIL-R.

Approximately 50 billion Jurkat cells were harvested by centrifugation (80 ml of cell pellet), washed once with PBS, then shock frozen on liquid nitrogen. Plasma membranes were isolated according to method number three described in Maeda et al., *Biochim. et Biophys. Acta,* 731:115, 1983; hereby incorporated by reference) with five modifications:

1. The following protease inhibitors were included in all solutions at the indicated concentrations: Aprotinin, 150 nM; EDTA, 5 mM; Leupeptin, 1 µM; pA-PMSF, 20 µM; Pefabloc, 500 µM; Pepstatin A, 1 µM; PMSF, 500 µM.
2. Dithiothreitol was not used.
3. DNAase was not used in the homogenization solution.
4. 1.25 ml of homogenization buffer was used per ml of cell pellet.
5. The homogenization was accomplished by five passages through a ground glass dounce homogenizer.

After isolation of the cell membranes, proteins were solubilized by resuspending the isolated membranes in 50 ml PBS containing 1% octylglucoside and all of the above mentioned protease inhibitors at the above indicated concentrations. The resulting solution was then repeatedly vortexed during a thirty-minute incubation at 4° C. The solution was then centrifuged at 20,000 rpm in an SW28 rotor in an LE-80 Beckman ultracentrifuge (Beckman Instruments, Inc., Palo Alto, Calif.) at 4° C. for 30 minutes to obtain the supernatant (the membrane extract).

Chromatography

The first step of purification of TRAIL-R out of the membrane extract prepared above was affinity chromatography. The membrane extract was first applied to an anti-Flag®M2 affi-gel column (10 mg of monoclonal antibody M2 coupled to 2 ml of Affi-gel beads) to adsorb any nonspecifically binding material. The flow-through was then applied to a Flag®-TRAIL affi-gel column (10 mg of recombinant protein coupled to 1 ml of affi-gel beads).

The Affi-gel support is an N-hydroxysuccinimide ester of a derivatized, crosslinked agarose gel bead (available from Biorad Laboratories, Richmond, Calif.). As discussed above, the Flag® peptide, Asp-Tyr-Lys-Asp-Asp-Asp-Asp-Lys, provides an epitope reversibly bound by specific monoclonal antibodies, enabling rapid assay and facile purification of expressed recombinant protein. M2 is a monoclonal antibody that binds Flag®. Monoclonal antibodies that bind the Flag® peptide, as well as other reagents for preparing and using Flag® fusion proteins, are available from Eastman Kodak Co., Scientific Imaging Systems Division, New Haven, Conn. Preparation of Flag®-TRAIL fusion proteins (comprising Flag® fused to a soluble TRAIL polypeptide) is further described in PCT application WO 97/01633, hereby incorporated by reference.

The column was washed with 25 ml of each of the following buffers, in the order indicated:

1. PBS containing 1% octylglucoside
2. PBS
3. PBS containing an additional 200 mM NaCl
4. PBS The bound material was eluted with 50 mM Na Citrate (pH 3) in 1 ml fractions and immediately neutralized with 300 µl of 1 M Tris-HCl (pH 8.5) per fraction. The TRAIL-binding activity of each fraction was determined by a TRAIL-R-specific ELISA as described below. Fractions with high TRAIL-binding activity were pooled, brought to 0.1% Trifluoroacetic acid (TFA), and subsequently chromatographed on a capillary reversed-phase HPLC column [500 µm internal diameter×25 cm fused silicone capillary column packed with 5 µm Vydac $C_4$ material (Vydac, Hesperia, Calif.)] using a linear gradient (2% per minute) from 0% to 100% acetonitrile in water containing 0.1% TFA. Fractions containing high TRAIL-binding activity are then determined as above, pooled, and, if desired, lyophilized.

TRAIL-R-specific ELISA:

Serial dilutions of TRAIL-R-containing samples (in 50 mM $NaHCO_3$, brought to pH 9 with NaOH) were coated onto Linbro/Titertek 96 well flat bottom E.I.A. microtitration plates (ICN Biomedicals Inc., Aurora, Ohio) at 100 µl/well. After incubation at 4° C. for 16 hours, the wells were washed six times with 200 µl PBS containing 0.05% Tween- 20 (PBS-Tween). The wells were then incubated with Flag®-TRAIL at 1 µg/ml in PBS-Tween with 5% fetal calf serum (FCS) for 90 minutes (100 µl per well), followed by washing as above. Next, each well was incubated with the anti-Flag® monoclonal antibody M2 at 1 µg/ml in PBS-Tween containing 5% FCS for 90 minutes (100 µl per well), followed by washing as above. Subsequently, wells were incubated with a polyclonal goat anti-mIgG1-specific horseradish peroxidase-conjugated antibody (a 1:5000 dilution of the commercial stock in PBS-Tween containing 5% FCS) for 90 minutes (100 µl per well). The HRP-conjugated antibody was obtained from Southern Biotechnology Associates, Inc., Birmingham, Ala. Wells then were washed six times, as above.

For development of the ELISA, a substrate mix [100 µl per well of a 1:1 premix of the TMB Peroxidase Substrate and Peroxidase Solution B (Kirkegaard Perry Laboratories, Gaithersburg, Md.)] was added to the wells. After sufficient color reaction, the enzymatic reaction was terminated by addition of 2 N $H_2SO_4$ (50 µl per well). Color intensity (indicating TRAIL-binding activity) was determined by measuring extinction at 450 nm on a V Max plate reader (Molecular Devices, Sunnyvale, Calif.).

EXAMPLE 2

Amino Acid Sequence (a) TRAIL-R purified from Jurkat cells

TRAIL-R protein isolated from Jurkat cells was digested with trypsin, using conventional procedures. Amino acid sequence analysis was conducted on one of the peptide fragments produced by the tryptic digest. The fragment was found to contain the following sequence, which corresponds to amino acids 327 to 333 of the sequence presented in SEQ ID NO:2: VPANEGD.

(b) TRAIL-R purified from PS-1 cells

TRAIL-R protein was also isolated from PS-1 cells. PS-1 is a human B cell line that spontaneously arose after lethal irradiation of human peripheral blood lymphocytes (PBLs). The TRAIL-R protein was digested with trypsin, using conventional procedures. Amino acid sequence analysis was conducted on peptide fragments that resulted from the tryptic digest. One of the fragments was found to contain the following sequence, which, like the fragment presented in (a), corresponds to amino acids 327 to 333 of the sequence presented in SEQ ID NO:2: VPANEGD.

EXAMPLE 3

DNA and Amino Acid Sequences

The amino acid sequence of additional tryptic digest peptide fragments of TRAIL-R was determined. Degenerate oligonucleotides, based upon the amino acid sequence of two of the peptides, were prepared. A TRAIL-R DNA fragment was isolated and amplified by polymerase chain reaction (PCR), using the degenerate oligonucleotides as 5' and 3' primers. The PCR was conducted according to conventional procedures, using cDNA derived from the PS-1 cell line described in example 2 as the template. The nucleotide sequence of the isolated TRAIL-R DNA fragment (excluding portions corresponding to part of the primers), and the amino acid sequence encoded thereby, are presented in FIG. 1 (SEQ ID NOS:3 and 4). The sequence of the entire TRAIL-R DNA fragment isolated by PCR corresponds to nucleotides 988 to 1164 of SEQ ID NO:1, which encode amino acids 330 to 388 of SEQ ID NO:2.

The amino acid sequence in SEQ ID NO:4 bears significant homology to the so-called death domains found in certain other receptors. The cytoplasmic region of Fas and TNF receptor type I each contain a death domain, which is associated with transduction of an apoptotic signal (Tartaglia et al. *Cell* 74:845, 1993; Itoh and Nagata, *J. Biol. Chem.* 268:10932, 1993). Thus, the sequence presented in SEQ ID NO:4 is believed to be found within the cytoplasmic domain of TRAIL-R.

A probe derived from the fragment isolated above was used to screen a cDNA library (human foreskin fibroblast-derived cDNA in λgt10 vector), and a human TRAIL-R cDNA was isolated. The nucleotide sequence of the coding region of this cDNA is presented in SEQ ID NO:1, and the amino acid sequence encoded thereby is shown in SEQ ID NO:2.

EXAMPLE 4

Monoclonal Antibodies That Bind TRAIL-R

This example illustrates a method for preparing monoclonal antibodies that bind TRAIL-R. Suitable immunogens that may be employed in generating such antibodies include, but are not limited to, purified TRAIL-R protein or an immunogenic fragment thereof such as the extracellular domain, or fusion proteins containing TRAIL-R (e.g., a soluble TRAIL-R/Fc fusion protein).

Purified TRAIL-R can be used to generate monoclonal antibodies immunoreactive therewith, using conventional techniques such as those described in U.S. Pat. No. 4,411,993. Briefly, mice are immunized with TRAIL-R immunogen emulsified in complete Freund's adjuvant, and injected in amounts ranging from 10–100 µg subcutaneously or intraperitoneally. Ten to twelve days later, the immunized animals are boosted with additional TRAIL-R emulsified in incomplete Freund's adjuvant. Mice are periodically boosted thereafter on a weekly to bi-weekly immunization schedule. Serum samples are periodically taken by retroorbital bleeding or tail-tip excision to test for TRAIL-R antibodies by dot blot assay, ELISA (Enzyme-Linked Immunosorbent Assay) or inhibition of TRAIL binding.

Following detection of an appropriate antibody titer, positive animals are provided one last intravenous injection of TRAIL-R in saline. Three to four days later, the animals are sacrificed, spleen cells harvested, and spleen cells are fused to a murine myeloma cell line, e.g., NS1 or preferably P3×63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified TRAIL-R by adaptations of the techniques disclosed in Engvall et al., *Immunochem.* 8:871, 1971 and in U.S. Pat. No. 4,703,004. A preferred screening technique is the antibody capture technique described in Beckmann et al., (*J. Immunol.* 144:4212, 1990) Positive hybridoma cells can be injected intraperitoneally into syngeneic BALB/c mice to produce ascites containing high concentrations of anti-TRAIL-R monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Protein A or Protein G can also be used, as can affinity chromatography based upon binding to TRAIL-R.

EXAMPLE 5

Northern Blot Analysis

The tissue distribution of TRAIL-R mRNA was investigated by Northern blot analysis, as follows. An aliquot of a radiolabeled probe (the same radiolabeled probe used to screen the cDNA library in example 3) was added to two different human multiple tissue Northern blots (Clontech, Palo Alto, Calif.; Biochain, Palo Alto, Calif.). Hybridization was conducted overnight at 63° C. in 50% formamide as previously described (March et al., *Nature* 315:641–647, 1985). The blots then were washed with 2×SSC, 0.1% SDS at 68° C. for 30 minutes. A glycerol-aldehyde-phosphate dehydrogenase (GAPDH) specific probe was used to standardize for RNA loadings.

A single transcript of 4.4 kilobases (kb) was present in all tissues examined, including spleen, thymus, peripheral blood lymphocytes (PBLs), prostate, testis, ovary, uterus, placenta, and multiple tissues along the gastro-intestinal tract (including esophagus, stomach, duodenum, jejunum/ileum, colon, rectum, and small intestine). The cells and tissues with the highest levels of TRAIL-R mRNA are PBLs, spleen, and ovary, as shown by comparison to control hybridizations with a GAPDH-specific probe.

EXAMPLE 6

Binding Assay

Full length human TRAIL-R was expressed and tested for the ability to bind TRAIL. The binding assay was conducted as follows.

A fusion protein comprising a leucine zipper peptide fused to the N-terminus of a soluble TRAIL polypeptide (LZ-TRAIL) was employed in the assay. An expression construct was prepared, essentially as described for preparation of the Flag®-TRAIL expression construct in Wiley et al. (*Immunity*, 3:673–682, 1995; hereby incorporated by reference), except that DNA encoding the Flag® peptide was replaced with a sequence encoding a modified leucine zipper that allows for trimerization. The construct, in expression vector pDC409, encoded a leader sequence derived from human cytomegalovirus, followed by the leucine zipper moiety fused to the N-terminus of a soluble TRAIL polypeptide. The TRAIL polypeptide comprised amino acids 95–281 of human TRAIL (a fragment of the extracellular domain), as described in Wiley et al. (supra). The LZ-TRAIL was expressed in CHO cells, and purified from the culture supernatant.

The expression vector designated pDC409 is a mammalian expression vector derived from the pDC406 vector described in McMahan et al. (*EMBO J.* 10:2821–2832, 1991; hereby incorporated by reference). Features added to pDC409 (compared to pDC406) include additional unique restriction sites in the multiple cloning site (mcs); three stop codons (one in each reading frame) positioned downstream of the mcs; and a T7 polymerase promoter, downstream of the mcs, that faciliates sequencing of DNA inserted into the mcs.

For expression of full length human TRAIL-R protein, the entire coding region (i.e., the DNA sequence presented in SEQ ID NO:1) was amplified by polymerase chain reaction (PCR). The template employed in the PCR was the cDNA clone isolated from a human foreskin fibroblast cDNA library, as described in example 3. The isolated and amplified DNA was inserted into the expression vector pDC409, to yield a construct designated pDC409-TRAIL-R.

CrmA protein was employed to inhibit apoptosis of host cells expressing recombinant TRAIL-R, as discussed above and in example 8. An expression vector designated pDC409-CrmA contained DNA encoding poxvirus CrmA in pDC409. The 38-kilodalton cowpox-derived protein that was subsequently designated CrmA is described in Pickup et al. (*Proc. Natl. Acad. Sci. USA* 83:7698–7702, 1986; hereby incorporated by reference).

CV-1/EBNA cells were co-transfected with pDC409-TRAIL-R together with pDC409-CrmA, or with pDC409-CrmA alone. The cells were cultured in DMEM supplemented with 10% fetal bovine serum, penicillin, streptomycin, and glutamine. 48 hours after transfection, cells were detached non-enzymatically and incubated with LZ-TRAIL (5 µg/ml), a biotinylated anti-LZ monoclonal antibody (5 µg/ml), and phycoerythrin-conjugated streptavidin (1:400), before analysis by fluorescence-activated cell scanning (FACS). The cytometric analysis was conducted on a FACscan (Beckton Dickinson, San Jose, Calif.).

The CV-1/EBNA cells co-transfected with vectors encoding TRAIL-R and CrmA showed significantly enhanced binding of LZ-TRAIL, compared to the cells transfected with the CrmA-encoding vector alone.

EXAMPLE 7

TRAIL-R Blocks TRAIL-Induced Apoptosis of Target Cells

TRAIL-R was tested for the ability to block TRAIL-induced apoptosis of Jurkat cells. The TRAIL-R employed in the assay was in the form of a fusion protein designated sTRAIL-R/Fc, which comprised the extracellular domain of human TRAIL-R, fused to the N-terminus of an Fc polypeptide derived from human IgG1.

CV1-EBNA cells were transfected with a recombinant expression vector comprising a gene fusion encoding the sTRAIL-R/Fc protein, in the pDC409 vector described in example 6, and cultured to allow expression of the fusion protein. The sTRAIL-R/Fc fusion protein was recovered from the culture supernatant. Procedures for fusing DNA encoding an IgG1 Fc polypeptide to DNA encoding a heterologous protein are described in Smith et al., (*Cell* 73:1349–1360, 1993); analogous procedures were employed herein.

A fusion protein designated TNF-R2-Fc, employed as a control, comprised the extracellular domain of the TNF receptor protein known as p75 or p80 TNF-R (Smith et al., *Science* 248:1019–1023, 1990; Smith et al. *Cell.*76:959–962, 1994), fused to an Fc polypeptide. A mouse monoclonal antibody that is a blocking antibody directed against human TRAIL, was employed in the assay as well.

Jurkat cells were incubated with varying or constant concentrations of LZ-TRAIL (the LZ-TRAIL fusion protein described in example 6), in the absence or presence of varying concentrations of sTRAIL-R-Fc, TNF-R2-Fc, or the TRAIL-specific monoclonal antibody. Cell death was quantitated using an MTT cell viability assay (MTT is 3-[4,5-dimethylthiazol-2-yl]-2,5-diphenyltetrazolium bromide), as previously described (Mosmann, *J. Immunol. Methods* 65:55–63, 1983). The results are shown in FIG. 2, which presents the percent cell death for Jurkat cells that were untreated (Δ) or were treated with varying (▲) or constant (○, ●, □, ■) concentrations of LZ-TRAIL (13 ng/ml) in the absence (●) or presence of varying concentrations of TRAIL-R2-Fc (■), TNF-R2-Fc (□), or the anti-TRAIL antibody (○). Varying concentrations for all substances started at 10 μg/ml and were serially diluted.

The anti-TRAIL monoclonal antibody and sTRAIL-R/Fc each blocked TRAIL-induced apoptosis in a dose dependent fashion, whereas TNFR2-Fc did not. Thus, the extracellular domain of TRAIL-R is capable of binding to TRAIL and inhibiting TRAIL-mediated apoptosis of target cells.

EXAMPLE 8

TRAIL-R-induced Apoptosis is Blocked by Caspase Inhibitors and FADD-DN

CV-1/EBNA cells were transfected, by the DEAE-dextran method, with expression plasmids for TRAIL-R (pDC409-TRAIL-R), together with a threefold excess of empty expression vector (pDC409) in the presence or absence of z-VAD-fmk (10 μM; in the culture medium), or together with a threefold excess of expression vector pDC409-CrmA, pDC409-p35, or pDC409-FADD-DN. In addition, 400 ng/slide of an expression vector for the *E. coli* lacz gene was co-transfected together with all DNA mixes. The transfected cells were cultured in chambers mounted on slides.

The mammalian expression vector pDC409, and the pDC409-TRAIL-R vector encoding full length human TRAIL-R, are described in example 6. The tripeptide derivative zVAD-fmk (benzyloxy-carbonyl-Val-Ala-Asp-fluoromethylketone) is available from Enzyme System Products, Dublin, Calif.

The 38-kilodalton cowpox-derived protein that was subsequently designated CrmA is described in Pickup et al. (*Proc. Natl. Acad. Sci. USA* 83:7698–7702, 1986; hereby incorporated by reference). Sequence information for CrmA is presented in FIG. 4 of Pickup et al., supra.

A 35-kilodalton protein encoded by *Autographa californica* nuclear polyhedrosis virus, a baculovirus, is described in Friesen and Miller (*J Virol.* 61:2264–2272, 1987; hereby incorporated by reference). Sequence information for this protein, designated baculovirus p35 herein, is presented in FIG. 5 of Friesen and Miller, supra.

FADD (also designated MORT1) is described in Boldin et al. (*J. Biol. Chem.* 270:7795–7798, 1995; hereby incorporated by reference). The protein referred to as FADD-DN (FADD dominant negative) is a C-terminal fragment of FADD that includes the death domain. DNA encoding FADD-DN, fused to an N-terminal Flag® epitope tag (described above), was inserted into the pDC409 expression vector described in example 6, to form pDC409-FADD-DN. The FADD-DN polypeptide corresponds to amino acids 117 through 245 of the MORT1 amino acid sequence presented in Boldin et al., supra.

48 hours after transfection, cells were washed with PBS, fixed with glutaraldehyde and incubated with X-gal (5-bromo-4-chloro-3-indoxyl-β-D-galactopyranoside). Cells expressing β-galactosidase stain blue. A decrease in the percentage of stained cells indicates loss of β-galactosidase expression, and correlates with death of cells that express the protein(s) co-transfected with the lacz gene.

Figure 3:
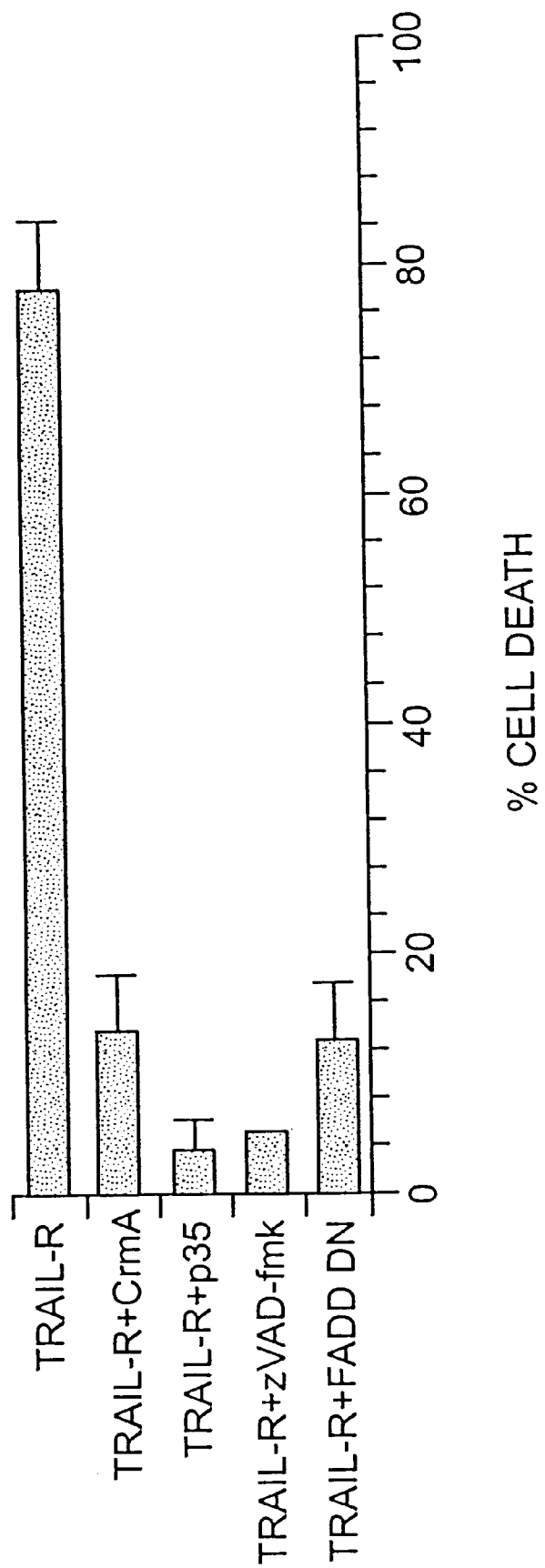
FIG. 3 presents the results of the experiment described in example 8. The indicated compounds were demonstrated to inhibit apoptosis of cells expressing TRAIL receptor.

The results are presented in FIG. 3, wherein the values plotted represent the mean and standard deviation of at least three separate experiments. Poxvirus CrmA, baculovirus p35, FADD-DN, and z-VAD-fmk each effectively reduced death of transfected cells expressing TRAIL-R.

What is claimed is:

1. A purified TRAIL-R polypeptide selected from the group consisting of:
   a) the TRAIL-R polypeptide of SEQ ID NO:2; and
   b) a fragment of the polypeptide of (a), wherein said fragment binds TRAIL.

2. A TRAIL-R polypeptide of claim 1, wherein said polypeptide comprises amino acids x to 440 of SEQ ID NO:2, wherein x represents an integer from 51 through 59.

3. A TRAIL-R polypeptide of claim 2, wherein said polypeptide comprises amino acids 54 to 440 of SEQ ID NO:2.

4. A TRAIL-R polypeptide of claim 1, wherein said fragment is a soluble TRAIL-R fragment.

5. A purified TRAIL-R polypeptide comprising an amino acid sequence that is at least 80% identical to the amino acid sequence presented in SEQ ID NO:2 wherein said polypeptide binds TRAIL.

6. A TRAIL-R polypeptide of claim 5, wherein said polypeptide comprises an amino acid sequence that is at least 90% identical to the amino acid sequence presented in SEQ ID NO:2.

7. A TRAIL-R polypeptide of claim 6, wherein said polypeptide comprises an amino acid sequence that is at least 95% identical to the amino acid sequence presented in SEQ ID NO:2.

8. An oligomer comprising from two to four TRAIL-R polypeptides of claim 5.

9. An oligomer comprising from two to four TRAIL-R polypeptides of claim 8.

10. A composition comprising a TRAIL-R polypeptide of claim 1, and a physiologically acceptable diluent, excipient, or carrier.

11. A composition comprising a TRAIL-R polypeptide of claim 4, and a physiologically acceptable diluent, excipient, or carrier.

12. A purified polypeptide encoded by a DNA comprising the nucleotide sequence of SEQ ID NO:1.

13. A purified polypeptide comprising amino acids x to 210 of SEQ ID NO:2, wherein x represents an integer from 51 to 59, wherein said polypeptide binds TRAIL.

14. A polypeptide of claim 13, wherein said polypeptide comprises amino acids 54 to 210 of SEQ ID NO:2.

15. A polypeptide of claim wherein said polypeptide comprises amino acids 52 to 210 of SEQ ID NO:2.

16. A polypeptide of claim 13, wherein said polypeptide is a soluble TRAIL-R polypeptide.

17. A polypeptide of claim 1, wherein said fragment comprises amino acids 94 to 178 SEQ ID NO:2.

18. A purified polypeptide comprising amino acids 94 to 178 of SEQ ID NO:2, wherein said polypeptide binds TRAIL.

19. A purified soluble TRAIL-R polypeptide comprising an amino acid sequence that is at least 80% identical to the sequence of amino acids 54 to 210 of SEQ ID NO:2, wherein said polypeptide binds TRAIL.

20. A polypeptide of claim 19, wherein the polypeptide comprises an amino acid sequence that is at least 90% identical to the sequence of amino acids 54 to 210 of SEQ ID NO:2.

21. A polypeptide of claim 19, wherein the polypeptide comprises an amino acid sequence that differs from the sequence of amino acids 54 to 210 of SEQ ID NO:2 by from one to ten amino acid deletions, insertions, or substitutions.

22. An oligomer comprising at least two polypeptides of claim 13.

23. An oligomer comprising at least two polypeptides of claim 14.

24. An oligomer comprising at least two polypeptides of claim 15.

25. An oligomer comprising at least two polypeptides of claim 16.

26. An oligomer comprising at least two polypeptides of claim 17.

27. An oligomer comprising at least two polypeptides of claim 18.

28. An oligomer comprising at least two polypeptides of claim 19.

29. An oligomer comprising at least two polypeptides of claim 20.

30. An oligomer comprising at least two polypeptides of claim 21.

31. An oligomer of claim 22, wherein the oligomer comprises two or three of said polypeptides.

32. An oligomer of claim 23, wherein the oligomer comprises two or three of said polypeptides.

33. An oligomer of claim 24, wherein the oligomer comprises two or three of said polypeptides.

34. An oligomer of claim 27, wherein the oligomer comprises two or three of said polypeptides.

35. An oligomer of claim 31, wherein the oligomer comprises two of said polypeptides.

36. A composition comprising a polypeptide of claim 13, and a physiologically acceptable diluent, excipient, or carrier.

37. A composition comprising a polypeptide of claim 18, and a physiologically acceptable diluent, excipient, or carrier.

38. A composition comprising an oligomer of claim 9, and a physiologically acceptable diluent, excipient, or carrier.

39. A composition comprising an oligomer of claim 22, and a physiologically acceptable diluent, excipient, or carrier.

40. A composition comprising an oligomer of claim 27, and a physiologically acceptable diluent, excipient, or carrier.

41. A composition comprising an oligomer of claim 31, and a physiologically acceptable diluent, excipient, or carrier.

* * * * *

UNITED STATES PATENT AND TRADEMARK OFFICE
CERTIFICATE OF CORRECTION

PATENT NO. : 6,642,358 B1
DATED : November 4, 2003
INVENTOR(S) : Charles Rauch and Henning Walczak It is certified that error appears in the above-identified patent and that said Letters Patent is hereby corrected as shown below:

Column 12,
Line 32, "interleukin4" should read -- interleukin-4 --.

Column 16,
Lines 61 and 66, "TRIAL" should read -- TRAIL --.

Column 17,
Lines 2, 6 and 7, "TRIAL" should read -- TRAIL --.
Line 6, "defection" should read -- defective --.

Column 18,
Line 21, "325" should read -- 3245 --.

Column 38,
Line 55, "5" should read -- 1 --.
Line 57, "8" should read -- 4 --.

Column 39,
Line 3, should read -- A polypeptide of claim 13 --.

Signed and Sealed this

Thirty-first Day of January, 2006

JON W. DUDAS
*Director of the United States Patent and Trademark Office*

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 1323 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vii) IMMEDIATE SOURCE:
      (B) CLONE: huTrail-R (ix) FEATURE:
      (A) NAME/KEY: CDS
      (B) LOCATION: 1..1323

(xi) SEQUENCE DESCRIPTION: SEQ ID NO: 1:

```
ATG GAA CAA CGG GGA CAG AAC GCC CCG GCC GCT TCG GGG GCC CGG AAA        48
Met Glu Gln Arg Gly Gln Asn Ala Pro Ala Ala Ser Gly Ala Arg Lys
 1               5                  10                  15

AGG CAC GGC CCA GGA CCC AGG GAG GCG CGG GGA GCC AGG CCT GGG CCC        96
Arg His Gly Pro Gly Pro Arg Glu Ala Arg Gly Ala Arg Pro Gly Pro
                20                  25                  30
```

```
CGG GTC CCC AAG ACC CTT GTG CTC GTT GTC GCC GCG GTC CTG CTG TTG      144
Arg Val Pro Lys Thr Leu Val Leu Val Val Ala Ala Val Leu Leu Leu
         35                  40                  45

GTC TCA GCT GAG TCT GCT CTG ATC ACC CAA CAA GAC CTA GCT CCC CAG      192
Val Ser Ala Glu Ser Ala Leu Ile Thr Gln Gln Asp Leu Ala Pro Gln
     50                  55                  60

CAG AGA GCG GCC CCA CAA CAA AAG AGG TCC AGC CCC TCA GAG GGA TTG      240
Gln Arg Ala Ala Pro Gln Gln Lys Arg Ser Ser Pro Ser Glu Gly Leu
 65                  70                  75                  80

TGT CCA CCT GGA CAC CAT ATC TCA GAA GAC GGT AGA GAT TGC ATC TCC      288
Cys Pro Pro Gly His His Ile Ser Glu Asp Gly Arg Asp Cys Ile Ser
                 85                  90                  95

TGC AAA TAT GGA CAG GAC TAT AGC ACT CAC TGG AAT GAC CTC CTT TTC      336
Cys Lys Tyr Gly Gln Asp Tyr Ser Thr His Trp Asn Asp Leu Leu Phe
             100                 105                 110

TGC TTG CGC TGC ACC AGG TGT GAT TCA GGT GAA GTG GAG CTA AGT CCG      384
Cys Leu Arg Cys Thr Arg Cys Asp Ser Gly Glu Val Glu Leu Ser Pro
         115                 120                 125

TGC ACC ACG ACC AGA AAC ACA GTG TGT CAG TGC GAA GAA GGC ACC TTC      432
Cys Thr Thr Thr Arg Asn Thr Val Cys Gln Cys Glu Glu Gly Thr Phe
     130                 135                 140

CGG GAA GAA GAT TCT CCT GAG ATG TGC CGG AAG TGC CGC ACA GGG TGT      480
Arg Glu Glu Asp Ser Pro Glu Met Cys Arg Lys Cys Arg Thr Gly Cys
145                 150                 155                 160

CCC AGA GGG ATG GTC AAG GTC GGT GAT TGT ACA CCC TGG AGT GAC ATC      528
Pro Arg Gly Met Val Lys Val Gly Asp Cys Thr Pro Trp Ser Asp Ile
                 165                 170                 175

GAA TGT GTC CAC AAA GAA TCA GGT ACA AAG CAC AGT GGG GAA GCC CCA      576
Glu Cys Val His Lys Glu Ser Gly Thr Lys His Ser Gly Glu Ala Pro
             180                 185                 190

GCT GTG GAG GAG ACG GTG ACC TCC AGC CCA GGG ACT CCT GCC TCT CCC      624
Ala Val Glu Glu Thr Val Thr Ser Ser Pro Gly Thr Pro Ala Ser Pro
         195                 200                 205

TGT TCT CTC TCA GGC ATC ATC ATA GGA GTC ACA GTT GCA GCC GTA GTC      672
Cys Ser Leu Ser Gly Ile Ile Ile Gly Val Thr Val Ala Ala Val Val
     210                 215                 220

TTG ATT GTG GCT GTG TTT GTT TGC AAG TCT TTA CTG TGG AAG AAA GTC      720
Leu Ile Val Ala Val Phe Val Cys Lys Ser Leu Leu Trp Lys Lys Val
225                 230                 235                 240

CTT CCT TAC CTG AAA GGC ATC TGC TCA GGT GGT GGT GGG GAC CCT GAG      768
Leu Pro Tyr Leu Lys Gly Ile Cys Ser Gly Gly Gly Gly Asp Pro Glu
                 245                 250                 255

CGT GTG GAC AGA AGC TCA CAA CGA CCT GGG GCT GAG GAC AAT GTC CTC      816
Arg Val Asp Arg Ser Ser Gln Arg Pro Gly Ala Glu Asp Asn Val Leu
             260                 265                 270

AAT GAG ATC GTG AGT ATC TTG CAG CCC ACC CAG GTC CCT GAG CAG GAA      864
Asn Glu Ile Val Ser Ile Leu Gln Pro Thr Gln Val Pro Glu Gln Glu
         275                 280                 285

ATG GAA GTC CAG GAG CCA GCA GAG CCA ACA GGT GTC AAC ATG TTG TCC      912
Met Glu Val Gln Glu Pro Ala Glu Pro Thr Gly Val Asn Met Leu Ser
     290                 295                 300

CCC GGG GAG TCA GAG CAT CTG CTG GAA CCG GCA GAA GCT GAA AGG TCT      960
Pro Gly Glu Ser Glu His Leu Leu Glu Pro Ala Glu Ala Glu Arg Ser
305                 310                 315                 320

CAG AGG AGG AGG CTG CTG GTT CCA GCA AAT GAA GGT GAT CCC ACT GAG     1008
Gln Arg Arg Arg Leu Leu Val Pro Ala Asn Glu Gly Asp Pro Thr Glu
                 325                 330                 335

ACT CTG AGA CAG TGC TTC GAT GAC TTT GCA GAC TTG GTG CCC TTT GAC     1056
Thr Leu Arg Gln Cys Phe Asp Asp Phe Ala Asp Leu Val Pro Phe Asp
```

```
                      340                    345                     350
TCC TGG GAG CCG CTC ATG AGG AAG TTG GGC CTC ATG GAC AAT GAG ATA      1104
Ser Trp Glu Pro Leu Met Arg Lys Leu Gly Leu Met Asp Asn Glu Ile
        355                     360                     365

AAG GTG GCT AAA GCT GAG GCA GCG GGC CAC AGG GAC ACC TTG TAC ACG      1152
Lys Val Ala Lys Ala Glu Ala Ala Gly His Arg Asp Thr Leu Tyr Thr
370                     375                     380

ATG CTG ATA AAG TGG GTC AAC AAA ACC GGG CGA GAT GCC TCT GTC CAC      1200
Met Leu Ile Lys Trp Val Asn Lys Thr Gly Arg Asp Ala Ser Val His
385                     390                     395                     400

ACC CTG CTG GAT GCC TTG GAG ACG CTG GGA GAG AGA CTT GCC AAG CAG      1248
Thr Leu Leu Asp Ala Leu Glu Thr Leu Gly Glu Arg Leu Ala Lys Gln
                405                     410                     415

AAG ATT GAG GAC CAC TTG TTG AGC TCT GGA AAG TTC ATG TAT CTA GAA      1296
Lys Ile Glu Asp His Leu Leu Ser Ser Gly Lys Phe Met Tyr Leu Glu
                420                     425                     430

GGT AAT GCA GAC TCT GCC ATG TCC TAA                                  1323
Gly Asn Ala Asp Ser Ala Met Ser  *
        435                     440

(2) INFORMATION FOR SEQ ID NO: 2:

(i) SEQUENCE CHARACTERISTICS:
        (A) LENGTH: 440 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Gln Arg Gly Gln Asn Ala Pro Ala Ala Ser Gly Ala Arg Lys
 1               5                  10                  15

Arg His Gly Pro Gly Pro Arg Glu Ala Arg Gly Ala Arg Pro Gly Pro
                20                  25                  30

Arg Val Pro Lys Thr Leu Val Leu Val Ala Ala Val Leu Leu Leu
            35                  40                  45

Val Ser Ala Glu Ser Ala Leu Ile Thr Gln Gln Asp Leu Ala Pro Gln
 50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Thr Lys His Ser Gly Glu Ala Pro
                180                 185                 190

Ala Val Glu Glu Thr Val Thr Ser Ser Pro Gly Thr Pro Ala Ser Pro
            195                 200                 205

Cys Ser Leu Ser Gly Ile Ile Ile Gly Val Thr Val Ala Ala Val Val
210                 215                 220
```

```
Leu Ile Val Ala Val Phe Val Cys Lys Ser Leu Leu Trp Lys Lys Val
225                 230                 235                 240

Leu Pro Tyr Leu Lys Gly Ile Cys Ser Gly Gly Gly Asp Pro Glu
            245                 250                 255

Arg Val Asp Arg Ser Ser Gln Arg Pro Gly Ala Glu Asp Asn Val Leu
            260                 265                 270

Asn Glu Ile Val Ser Ile Leu Gln Pro Thr Gln Val Pro Glu Gln Glu
            275                 280                 285

Met Glu Val Gln Glu Pro Ala Glu Pro Thr Gly Val Asn Met Leu Ser
            290                 295                 300

Pro Gly Glu Ser Glu His Leu Leu Glu Pro Ala Glu Ala Glu Arg Ser
305                 310                 315                 320

Gln Arg Arg Arg Leu Leu Val Pro Ala Asn Glu Gly Asp Pro Thr Glu
            325                 330                 335

Thr Leu Arg Gln Cys Phe Asp Asp Phe Ala Asp Leu Val Pro Phe Asp
            340                 345                 350

Ser Trp Glu Pro Leu Met Arg Lys Leu Gly Leu Met Asp Asn Glu Ile
            355                 360                 365

Lys Val Ala Lys Ala Glu Ala Ala Gly His Arg Asp Thr Leu Tyr Thr
            370                 375                 380

Met Leu Ile Lys Trp Val Asn Lys Thr Gly Arg Asp Ala Ser Val His
385                 390                 395                 400

Thr Leu Leu Asp Ala Leu Glu Thr Leu Gly Glu Arg Leu Ala Lys Gln
            405                 410                 415

Lys Ile Glu Asp His Leu Leu Ser Ser Gly Lys Phe Met Tyr Leu Glu
            420                 425                 430

Gly Asn Ala Asp Ser Ala Met Ser
            435                 440

(2) INFORMATION FOR SEQ ID NO: 3:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: internal (vii) IMMEDIATE SOURCE:
         (B) CLONE: huTrail-R frag (ix) FEATURE:
         (A) NAME/KEY: CDS
         (B) LOCATION: 3..155

(xi) SEQUENCE DESCRIPTION: SEQ ID NO: 3:

CT GAG ACT CTG AGA CAG TGC TTC GAT GAC TTT GCA GAC TTG GTG CCC        47
   Glu Thr Leu Arg Gln Cys Phe Asp Asp Phe Ala Asp Leu Val Pro
   1               5                   10                  15

TTT GAC TCC TGG GAG CCG CTC ATG AGG AAG TTG GGC CTC ATG GAC AAT       95
Phe Asp Ser Trp Glu Pro Leu Met Arg Lys Leu Gly Leu Met Asp Asn
                20                  25                  30

GAG ATA AAG GTG GCT AAA GCT GAG GCA GCG GGC CAC AGG GAC ACC TTG      143
```

-continued

```
Glu Ile Lys Val Ala Lys Ala Glu Ala Ala Gly His Arg Asp Thr Leu
            35                  40                  45

TNC ACN ATG CTG AT                                              157
Xaa Thr Met Leu
        50
```

(2) INFORMATION FOR SEQ ID NO: 4:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO: 4:

```
Glu Thr Leu Arg Gln Cys Phe Asp Asp Phe Ala Asp Leu Val Pro Phe
 1               5                  10                  15

Asp Ser Trp Glu Pro Leu Met Arg Lys Leu Gly Leu Met Asp Asn Glu
            20                  25                  30

Ile Lys Val Ala Lys Ala Glu Ala Ala Gly His Arg Asp Thr Leu Xaa
            35                  40                  45

Thr Met Leu
    50
```

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vii) IMMEDIATE SOURCE:
        (B) CLONE: FLAG peptide (xi) SEQUENCE DESCRIPTION: SEQ ID NO: 5:

```
Asp Tyr Lys Asp Asp Asp Asp Lys
 1               5
```